(12) United States Patent
Meier

(10) Patent No.: US 9,022,940 B2
(45) Date of Patent: May 5, 2015

(54) HANDHELD IMAGING DEVICES AND RELATED METHODS

(75) Inventor: Joseph H. Meier, McKinney, TX (US)

(73) Assignee: Joseph H. Meier, McKinney, TX (US)

( * ) Notice: Subject to any disclaimer, the term of this patent is extended or adjusted under 35 U.S.C. 154(b) by 1116 days.

(21) Appl. No.: 12/837,342

(22) Filed: Jul. 15, 2010

(65) Prior Publication Data

US 2010/0312120 A1    Dec. 9, 2010

Related U.S. Application Data

(63) Continuation-in-part of application No. 12/179,194, filed on Jul. 18, 2008, now abandoned.

(60) Provisional application No. 61/352,350, filed on Jun. 7, 2010.

(51) Int. Cl.
*A61B 8/14* (2006.01)
*A61B 8/00* (2006.01)
*A61B 8/08* (2006.01)

(52) U.S. Cl.
CPC .............. *A61B 8/00* (2013.01); *A61B 8/0833* (2013.01); *A61B 8/0841* (2013.01); *A61B 8/4281* (2013.01); *A61B 8/4422* (2013.01); *A61B 8/4427* (2013.01); *A61B 8/4472* (2013.01); *A61B 8/4477* (2013.01); *A61B 8/462* (2013.01); *A61B 8/54* (2013.01)

(58) Field of Classification Search
CPC ............ A61B 2017/3413; A61B 17/3043; A61B 2019/5276; A61B 8/00; A61B 8/0833; A61B 8/0841; A61B 8/4281; A61B 8/4422; A61B 8/4427; A61B 8/4472; A61B 8/4477; A61B 8/462; A61B 8/54; G01S 15/8925
USPC ............ 600/407–472; 128/916; 707/1; 705/2
See application file for complete search history.

(56) References Cited

U.S. PATENT DOCUMENTS

| | | |
|---|---|---|
| 4,401,124 A | 8/1983 | Guess et al. |
| 4,407,294 A | 10/1983 | Vilkomerson |
| 5,070,882 A | 12/1991 | Bui et al. |

(Continued)

OTHER PUBLICATIONS

SonoSite; 180PLUS; http://www.sonosite.com/downloads/180PLUS_Brochures.pdf; 2005; 2 pages.

(Continued)

*Primary Examiner* — Elmer Chao
(74) *Attorney, Agent, or Firm* — Bryan Cave LLP

(57) ABSTRACT

A monitoring device can be configured to facilitate intra-tissue inspection of a probe at a target region, the monitoring device comprising a housing, a transducer coupled to the housing, and a display coupled to the transducer and to the housing. The transducer can comprise a first transducer array aligned to scan a longitudinal plane of the target region, and a second transducer array aligned to scan a transverse plane of the target region. The display can be configured to receive information derived from the first and second transducers to present an image of at least one of the longitudinal plane or the transverse plane, and to present at the image a probe point highlight of a probe point of the probe. Other examples, embodiments, and related methods are described herein.

24 Claims, 14 Drawing Sheets

(56) References Cited

U.S. PATENT DOCUMENTS

| | | | |
|---|---|---|---|
| 5,329,927 | A | 7/1994 | Gardineer et al. |
| 6,251,073 | B1 | 6/2001 | Imran et al. |
| 6,540,685 | B1 | 4/2003 | Rhoads et al. |
| 6,569,102 | B2 | 5/2003 | Imran et al. |
| 6,755,789 | B2 | 6/2004 | Stringer et al. |
| 7,214,191 | B2 | 5/2007 | Stringer et al. |
| 7,241,267 | B2 | 7/2007 | Furia |
| 7,244,234 | B2 | 7/2007 | Ridley et al. |
| 2003/0220573 | A1 | 11/2003 | Imran et al. |
| 2004/0158154 | A1* | 8/2004 | Hanafy et al. ............ 600/446 |
| 2005/0020919 | A1 | 1/2005 | Stringer et al. |
| 2005/0085730 | A1* | 4/2005 | Flesch et al. ............ 600/459 |
| 2006/0184029 | A1 | 8/2006 | Haim et al. |
| 2006/0184034 | A1 | 8/2006 | Haim et al. |
| 2007/0016030 | A1 | 1/2007 | Stringer |
| 2007/0182950 | A1 | 8/2007 | Arlinsky |
| 2008/0015442 | A1* | 1/2008 | Watson et al. ............ 600/459 |
| 2008/0281206 | A1* | 11/2008 | Bartlett et al. ............ 600/459 |
| 2009/0177114 | A1* | 7/2009 | Chin et al. ............ 600/565 |

OTHER PUBLICATIONS

PunctSURE; Ultrasonic Vascular Imaging System, Operation Manual; 2003; 32 pages.

Siemens; Revolutionize the Way You Work; The First Pocket Ultrasound System; www.medical.siemens.com/siemens/en_USgg_us_FBAs/files/brochures/Acuson/P10_datasheet.pdf; Nov. 2007; 2 pages.

Escalon; VascuView; http://www.escalonmed.com/eva/vvprod.html; Apr. 4, 2008; 1 page.

Arrow International; InView; www.arrowint.com/documents/pdf/literature/inv-rf0707.pdf; 2007; 2 pages.

CNN.com; Ultrasound may mean end to classic stethoscope; http://www.cnn.com/2003/HEALTH/08/27/ultra.stethoscope/index.html; Jul. 17, 2008; 3 pages.

SonoSite 180PLUS / OVERVIEW http://www.sonosite.com/products/180plus/; Jul. 17, 2008; 4 pages.

Disposable Echotip Coaxial Needle Biopsy Set; http://web.archive.org/web/20070517204457/http://www.coodmedical.com/; Cook Medical 2007; 1 page.

* cited by examiner

US 9,022,940 B2

HANDHELD IMAGING DEVICES AND RELATED METHODS

CROSS-REFERENCE TO RELATED APPLICATION

This patent application claims priority to U.S. Patent Application No. 61/352,350, filed on Jun. 7, 2010, and is a continuation in part application of U.S. patent application Ser. No. 12/176,194, filed on Jul. 18, 2008. The disclosures of the referenced applications are incorporated herein by reference.

TECHNICAL FIELD

This disclosure relates generally to imaging devices, and relates more particularly to handheld imaging devices and methods of manufacture for handheld imaging devices.

BACKGROUND

The use of non-invasive monitoring systems, such as ultrasound devices, to produce real-time images of blood vessels, organs, bones, nerves, tumors, and other target structures under the skin or other layers of tissue in patients has advanced the techniques used for interacting with such target structures. Procedures for epidural placements, lumbar punctures, nerve blockings, and the cannulation of vascular vessels, among other procedures, have been accordingly advanced. For example, prior to the development of such systems, medical practitioners attempting to cannulate a vascular vessel had to rely on approximations of the predicted locations of such target structures, without any internal visual aids to guide the cannulation process through the interior of the patient. This cannulation technique can produce unwanted results, such as the puncturing of wrong vascular vessels or structures, and/or repeated painful attempts to locate and cannulate the correct structure.

Although technology has advanced the monitoring process, cannulation still requires hand/eye coordination between the images scanned by a monitoring system and a needle or probe as it is inserted by the hand of the medical practitioner into a target area of a patient. Accordingly, a need exists for a monitoring device that can present real-time internal images of the cannulation process proximate to, and aligned with, the target area and internal target structure to, therefore, assist the hand/eye coordination of the medical practitioner during the monitoring and/or cannulation process.

BRIEF DESCRIPTION OF THE DRAWINGS

The invention will be better understood from a reading of the following detailed description of examples of embodiments, taken in conjunction with the accompanying figures in the drawings in which.

Figure 1:
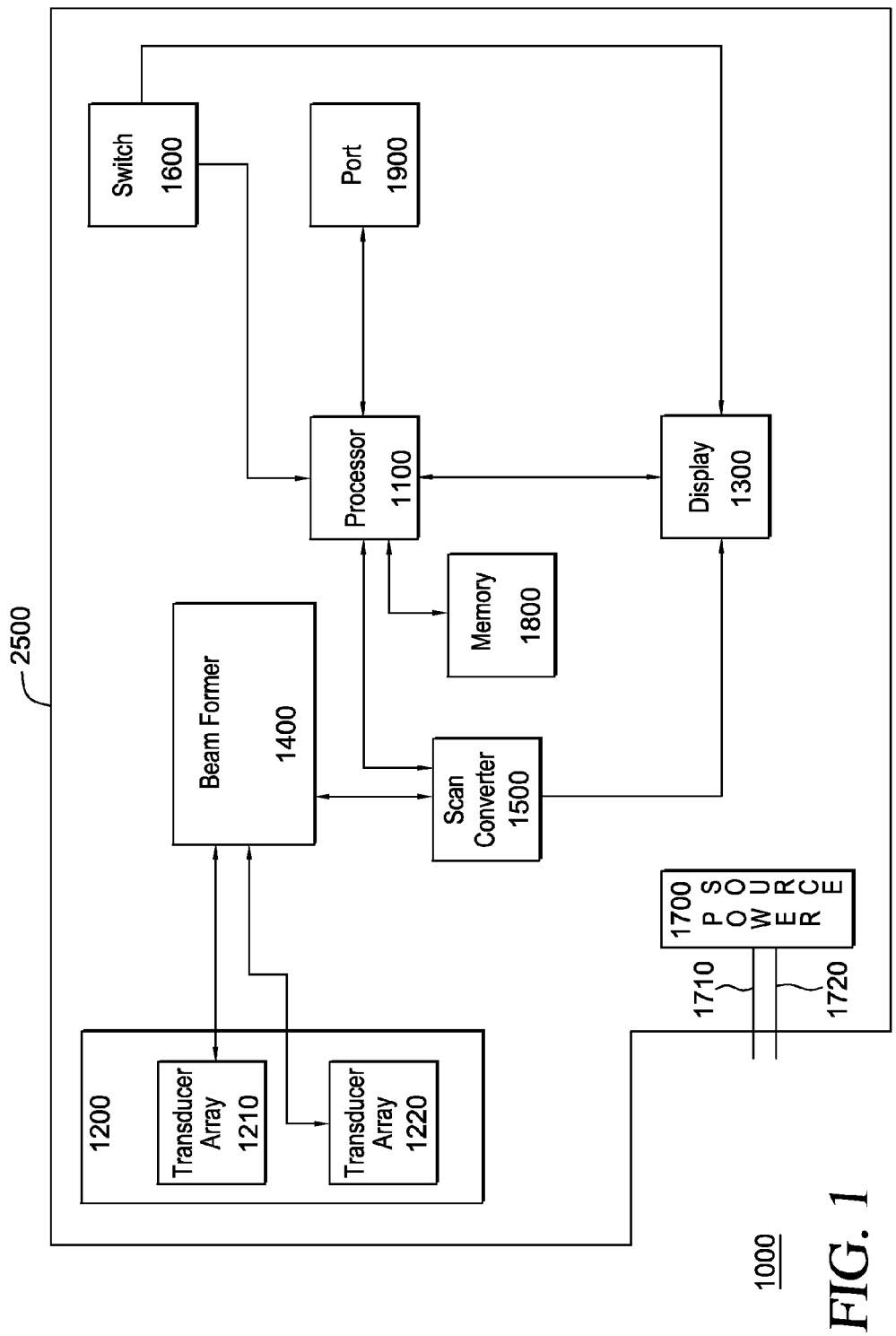
FIG. 1 illustrates a block diagram of a monitoring device.

For simplicity and clarity of illustration, the drawing figures illustrate the general manner of construction, and descriptions and details of well-known features and techniques may be omitted to avoid unnecessarily obscuring the invention. Additionally, elements in the drawing figures are not necessarily drawn to scale. For example, the dimensions of some of the elements in the figures may be exaggerated relative to other elements to help improve understanding of examples of embodiments. The same reference numerals in different figures denote the same elements.

The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments of the invention described herein are, for example, capable of operation in sequences other than those illustrated or otherwise described herein. Furthermore, the terms "include," and "have," and any variations thereof, are intended to cover a non-exclusive inclusion, such that a process, method, article, or apparatus that comprises a list of elements is not necessarily limited to those elements, but may include other elements not expressly listed or inherent to such process, method, article, or apparatus.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments of the invention described herein are, for example, capable of operation in other orientations than those illustrated or otherwise described herein. The term "coupled," as used herein, is defined as directly or indirectly connected in an electrical, physical, mechanical, or other manner.

DETAILED DESCRIPTION OF EXEMPLARY EMBODIMENTS

In one embodiment, an ultrasound imaging device is configured to facilitate sub-dermal monitoring. The ultrasound imaging device comprises a handheld housing, a processor within the handheld housing, a beamformer coupled to the processor, a transducer assembly coupled to the handheld housing and to at least one of the beamformer and the processor, a scan converter coupled to the transducer assembly, a display coupled to the handheld housing and coupled to at least one of the scan converter and the processor, a switch mechanism coupled to the processor, a rechargeable power source coupled to the handheld housing, a communications port coupled to the processor, a central pointer aligned with a center of the display, and a needle guide coupled to the handheld housing proximate to the transducer assembly. The transducer assembly comprises a first transducer array coupled to the processor and aligned along a first axis, and a second transducer array coupled to the processor and aligned along a second axis different from the first axis, where the first transducer array and the second transducer array are configured to produce an overlapping scan at a target focus point. The first axis is longitudinal to the target focus point; the second axis is transverse to the target focus point; and the first transducer array and the second transducer array are substantially perpendicular to each other. The first transducer array comprises transducer elements configured to scan images along the first axis, and the second transducer array comprises transducer elements configured to scan images along the second axis. The first and second transducer arrays are capable of concurrently imaging the target focus point. The rechargeable power source is cordless and configured to power the monitoring device uninterrupted for at least approximately a half-hour, and the ultrasound imaging device is configured for single-handed operation.

In another embodiment, a monitoring device can be configured to facilitate intra-tissue inspection of a needle at a target region, the monitoring device comprising a housing, a transducer coupled to the housing, and a display coupled to the transducer and to the housing. The transducer can comprise a first transducer array aligned to scan a longitudinal plane of the target region, and a second transducer array aligned to scan a transverse plane of the target region. The display can be configured to receive information derived from the first and second transducers to present an image of at least one of the longitudinal plane or the transverse plane, and to present at the image a needle point highlight of a needle point of the needle.

In one embodiment, an ultrasound imaging device can be configured to facilitate sub-dermal monitoring of a probe inserted into a target zone. The ultrasound imaging device can comprise a handheld housing, a processor within the handheld housing, a transducer assembly coupled to the handheld housing and to the processor, a scan converter coupled to the transducer assembly, a display coupled to the handheld housing and coupled to at least one of the scan converter or the processor, a rechargeable power source coupled to the handheld housing, a central pointer aligned with a center of the display, and a probe guide coupled to the handheld housing proximate to the transducer assembly. The transducer assembly can comprise a first transducer array coupled to the processor and aligned along a first axis, and a second transducer array coupled to the processor and aligned along a second axis different than the first axis, where the first axis is longitudinal to the target zone, and the second axis is transverse to the target zone, and the first transducer array and the second transducer array are substantially perpendicular to each other. The first transducer array can comprise transducer elements configured to scan along the first axis, and the second transducer array can comprise transducer elements configured to scan along the second axis. The rechargeable power source can be cordless and configured to power the monitoring device uninterrupted for at least approximately a half-hour. The ultrasound imaging device is configured for single-handed operation, and the display is configured to present an image comprising a transverse view of a transverse cross-section of the target zone along the second axis, and a probe point highlight of a probe point of the probe.

In one example, a monitoring device can be configured to facilitate intra-tissue inspection of a probe at a target region. The monitoring device can comprise a housing, a transducer coupled to the housing, and a display coupled to the transducer and to the housing. The transducer can comprise a first transducer array aligned to scan a longitudinal plane of the target region, and a second transducer array aligned to scan a transverse plane of the target region. The display can be configured to receive information derived from the first and second transducers to (1) present an image of at least one of the longitudinal plane or the transverse plane, and (2) present at the image a probe point highlight of a probe point of the probe.

In one example, a method for providing a monitoring device can comprise providing a housing, providing a transducer coupled to the housing, and providing a display coupled to the transducer and to the housing. Providing the transducer can comprise providing a first transducer array aligned to scan a longitudinal plane of a target region, the target region being subdermal, and providing a second transducer array aligned to scan a transverse plane of the target region. The display can be provided to present an image of at least one of a longitudinal plane view derived from the first transducer array, or a transverse plane view derived from the second transducer array, and to present at the image a probe point highlight of a probe point of a probe.

In one example, a needle can comprise an interior surface, an exterior surface, a needle tip portion comprising a bevel, and one or more indentations configured to enhance ultrasonic beam reflections off the needle tip portion. A first indentation of the one or more indentations can be located at the interior surface adjacent to the bevel of the tip portion.

Other examples, embodiments, and related methods are further described below. Such examples, embodiments, and related methods may be found in the figures, in the claims, and/or in the description of the present application.

Figure 2:
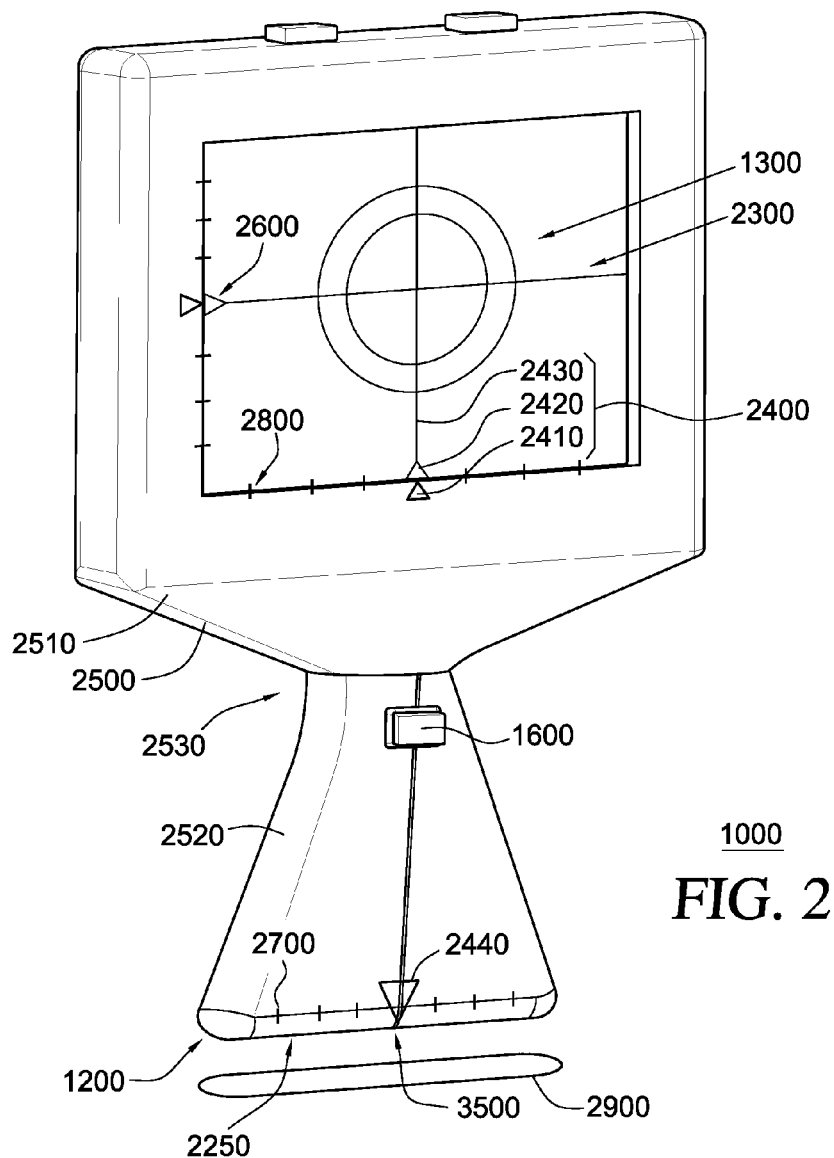
FIG. 2 illustrates a front perspective view of the monitoring device of FIG. 1.
Figure 3:
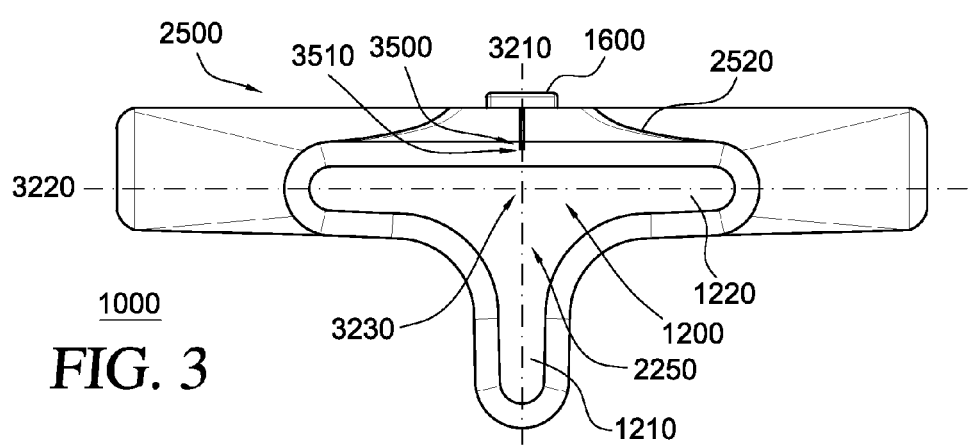
FIG. 3 illustrates a bottom view of the monitoring device of FIG. 1.
Figure 5:
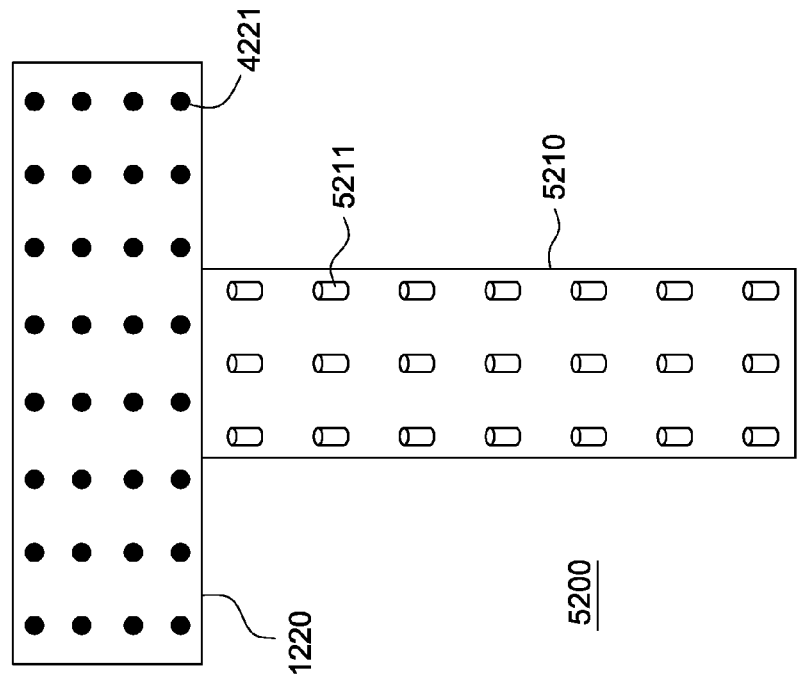
FIG. 5 illustrates a bottom view of another transducer for the monitoring device of FIG. 1.
Figure 4:
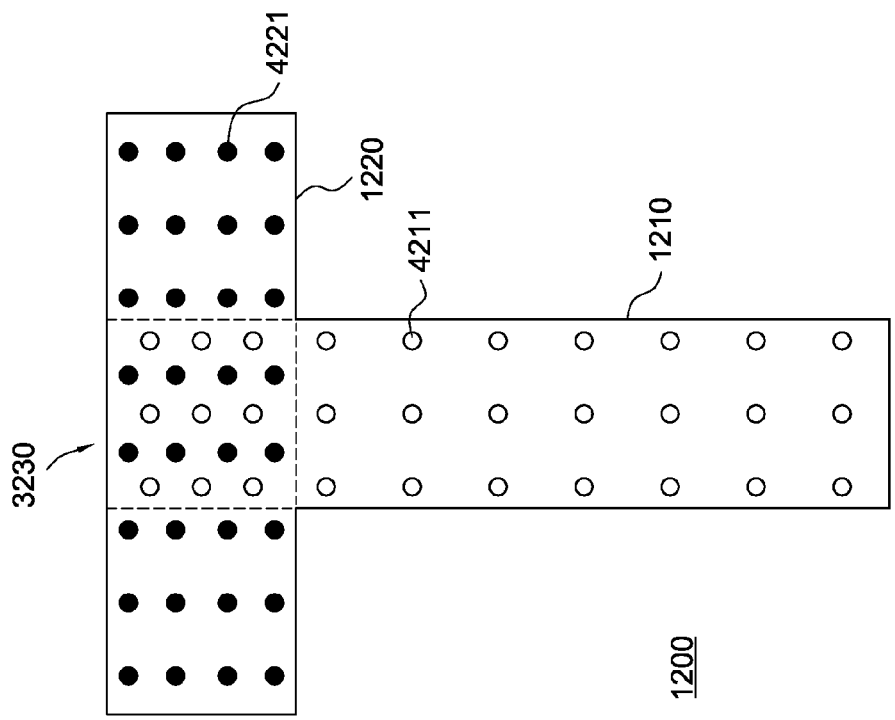
FIG. 4 illustrates a bottom view of a transducer for the monitoring device of FIG. 1.

Turning over to the figures, FIG. 1 illustrates a block diagram of a monitoring device 1000. FIG. 2 illustrates a front perspective view of monitoring device 1000. FIG. 3 illustrates a bottom view of monitoring device 1000. FIG. 4 illustrates a bottom view of transducer 1200 of monitoring device 1000. FIG. 5 illustrates a bottom view of transducer 5200 of monitoring device 1000.

In some embodiments, monitoring device 1000 can be used in the medical field for intra-tissue or sub-dermal inspection on a patient. As an example, monitoring device 1000 can be used to facilitate non-invasive imaging of vascular vessels, such as veins and arteries, through skin and/or other tissue. In one example, such imaging can be useful to guide a medical practitioner while cannulating a vascular vessel, allowing the medical practitioner to align, position, and guide a needle into the vascular vessel. In some embodiments, the needle can comprise a probe and/or a catheter.

In the present embodiment, monitoring device 1000 comprises processor 1100 within housing 2500. Processor 1100 can comprise, for example, a microprocessor such as a general microprocessor for personal computers, and/or a specialized microprocessor for a specific implementation such as analog and mixed signal operations. Monitoring device 1000 can also comprise memory 1800 coupled to processor 1100. Memory 1800 can be used to store software instructions for operating monitoring device 1000, and/or information such as images scanned using monitoring device 1000. In the same or a different embodiment, memory 1800 can comprise non-volatile memory, such as flash memory, and/or magnetic storage such as hard disks. In some embodiments, memory 1800 can comprise removable memory devices, such as SD (Secure Digital) cards. In a different embodiment, processor 1100 and memory 1800 can be combined to form a microcontroller.

Monitoring device 1000 also comprises display 1300 coupled to processor 1100 and to housing 2500. In some embodiments, display 1300 can comprise a width of approximately 3 to 8 centimeters, and/or a height of approximately 2 to 5 centimeters. In one embodiment, display 1300 can comprise at least one of a Liquid Crystal Display (LCD), a touch-screen display, and a Thin Film Transistor (TFT) display. In the same or a different embodiment, display 1300 can be configured to present a data entry screen, where information such as a patient's name and/or a medical record number can be entered by interacting with the data entry screen. In the same or a different embodiment, the data entry screen can be configured to accept input from a touch-screen coupled to display 1300, a keypad coupled to monitoring device 1000, and/or a point and click mechanism. In the same or a different embodiment, information entered into the data entry screen can be stored into memory 1800, and/or can be correlated to information or images stored in memory 1800.

Display 1300 can be configured to be aligned with, and visible through, translucent portion 2300 (FIG. 2) of housing 2500, where translucent portion 2300 can comprise a translucent material, transparent material, or a cutout. In some embodiments, display 1300 can also be coupled to a graphics adapter (not shown). In the same or a different embodiment, the graphics adapter can be part of processor 1100. In a different embodiment, monitoring device 1000 can also comprise additional displays similar to display 1300.

Monitoring device 1000 also comprises transducer 1200 coupled to processor 1100 and to housing 2500. In the present embodiment, transducer 1200 comprises transducer arrays 1210 and 1220 coupled to processor 1100, where transducer array 1210 is aligned along axis 3210 (FIG. 3), and where transducer array 1220 is aligned along axis 3220 (FIG. 3) of scanning surface 2250 (FIG. 2). In the same or a different embodiment, transducer arrays 1210 and 1220 can be ultrasonic transducer arrays comprising piezoelectric elements configured to emit ultrasonic beams and/or to detect reflections of the ultrasonic beams.

Transducer arrays 1210 and 1220 are configured to produce different but overlapping scans (not shown), where an image can be presented on display 1300 based on readings from the overlapping scan. In the present embodiment, as more clearly seen in FIG. 4, transducer arrays 1210 and 1220 overlap at transducer junction 3230 of transducer 1200, where respective elements 4211 and 4221 of transducer arrays 1210 and 1220 coincide. In the same or a different embodiment, one or more of elements 4211 and 4221 that are proximate to transducer junction 3230 can be shared by both transducer arrays 1210 and 1220. Portions of transducer arrays 1210 and 1220 overlap substantially perpendicular to each other. In addition, beams emitted by elements 4211 and 4221 are substantially perpendicular to scanning surface 2250. As also seen in FIG. 4, other portions of transducer arrays 1210 and 1220 do not overlap with each other.

In a different embodiment, as more clearly seen in FIG. 5, monitoring device 1000 can comprise transducer 5200 with transducer arrays 5210 and 1220. Transducer 5200 can also produce different but overlapping scans similar to the overlapping scans produced by transducer 1200, but transducer 5200 differs in that there is no transducer junction because transducer arrays 5210 and 1220 do not physically overlap. Instead, transducer array 5210 comprises elements 5211 that are configured to transmit and/or detect ultrasonic beams at an angle such as to overlap with beams transmitted by elements 4221 of transducer array 1220. In a different embodiment, elements 4221 are modified to transmit and/or detect ultrasonic beams at an angle to overlap with beams transmitted by elements 5211, which are modified to transmit beams substantially perpendicular to scanning surface 2250. In another embodiment, both elements 4221 and 5211 are angled.

Returning to the embodiment of FIGS. 1-4, transducer 1200 is at least partially enclosed by housing 2500. Similarly, display 1300 is at least partially enclosed by housing 2500. In the same or a different embodiment, transducer 1200 and display 1300 can be integrated with housing 2500 such as to form a single handheld unit out of monitoring device 1000, with no external cables to interconnect display 1300 and/or transducer 1200 to housing 2500 and/or processor 1100. In the same or a different embodiment, housing 2500 can comprise materials such as metal, acrylics, polycarbonates, and other rigid or semi-rigid plastics. As used herein, the term "integrated" allows for interchangeable portions of monitoring device 1000. For example, in the same or a different embodiment, housing 2500 can be integrated with a different transducer, such as transducer 5200, which is replaceable or interchangeable with transducer 1200.

In the present embodiment, as shown in FIG. 1, monitoring device 1000 comprises beamformer 1400 coupled to transducer 1200. In addition, processor 1100 couples to transducer 1200 through beamformer 1400. In the present example, beamformer 1400 is configured to control the timing, strength, angle, amplitude, and/or phase of ultrasound signals transmitted by transducer arrays 1210 and 1220. In the same or a different example, beamformer 1400 can be configured to control transducer arrays 1210 and 1220 to receive signals predominantly from a chosen angular direction.

Continuing with the present embodiment, monitoring device 1000 also comprises scan converter 1500 coupled to beamformer 1400 and to display 1300. In some embodiments, scan converter 1500 can be coupled to display 1300 via processor 1100. Scan converter 1500 can be used to convert information from ultrasound signals received by transducer arrays 1210 and 1220 into an image format that can be displayed on, for example, display 1300. In the present embodiment, beamformer 1400 can comprise at least one of a B-mode, F-mode, and a D-mode acquisition mode.

As described above, monitoring device 1000 can be used to image through target location 2900 (FIG. 2), where target location 2900 can be under the skin surface of a patient or person. In the present embodiment, axis 3210 (FIG. 3) is longitudinal to target location 2900, while axis 3220 is transverse to target location 2900. In addition, display 1300 is substantially parallel to axis 3220. Transducer 1200 is configured to scan a set of readings of target location 2900 using at least a portion of transducer array 1210, while simultaneously scanning a different set of readings of target location 2900 using at least a portion of transducer array 1220. In the current embodiment, at least one of transducer arrays 1210 and 1220 is configured to scan a depth of field of up to approximately 10 centimeters.

In the same or a different embodiment, at least one of transducer arrays 1210 and 1220 is configured to scan a span of up to approximately 4 to 5 cm. In the same or a different embodiment, at least one of transducer arrays 1210 and 1220 can be configured to scan at a transducer frequency of approximately between 2 and 50 MHz.

In the present embodiment, monitoring device 1000 also comprises a switch mechanism 1600 coupled to processor 1100. Switch Mechanism 1600 is configured to deactivate transducer array 1220 and activate transducer array 1210 in response to a first setting of switch mechanism 1600. In addition, switch mechanism 1600 is configured to deactivate transducer array 1210 and activate transducer array 1220 in response to a second setting of switch mechanism 1600. In the present embodiment, the settings of switch mechanism 1600 are recognized by processor 1000, which causes transducer arrays 1210 and/or 1220 to activate or deactivate accordingly and which changes the image(s) shown on display 1300. In a different embodiment, switch mechanism 1600 can communicate more directly with transducer arrays 1210 and/or 1220, such as through beamformer 1400, to activate or deactivate transducer arrays 1210 and/or 1220 accordingly.

In the same or a different embodiment, monitoring device 1000 is configured for one-handed operation. For example, monitoring device 1000 can be configured to allow a hand to grab around portion 2520 (FIG. 2) of housing 2500, such that switch mechanism 1600 can be still operable by a finger (e.g., a thumb) of the same hand without releasing portion 2520. In addition, monitoring device 1000 can be configured for non-dominant handed operation. Such non-dominant handed configuration can be advantageous, for example, to free-up a user's dominant hand to cannulate a vascular vessel monitored through monitoring device 1000. In some embodiments, a weight of monitoring device 1000 is between approximately 0.3 and 0.7 kilograms.

In some embodiments, monitoring device 1000 can comprise other switches or buttons to control other operations or features of monitoring device 1000. Such other switches can comprise one or more of an on/off control, a gain control, a depth control, a focus control, a brightness control, and/or a contrast control.

Display 1300, in the current embodiment of monitoring device 1000, is configured to present images correlated to readings from transducer array 1210 in response to one setting of switch mechanism 1600. Display 1300 is also configured to present images correlated to a set of readings from transducer array 1220 in response to a different setting of switch mechanism 1600. In the present embodiment, because display 1300 is sized to allow monitoring device 1000 to be handheld, it can be clearer for display 1300 to present images from only one of transducer arrays 1210 and 1220 at a time. Switch mechanism 1600 can therefore be used to toggle the source of images on display 1300 from array 1210 to 1220, and vice-versa. In a different embodiment, however, monitoring device 1000 can be configured to simultaneously present images correlated to readings from transducer array 1210 on one portion of display 1300, and images correlated to readings from transducer array 1220 on another portion of display 1300.

In the same or a different embodiment, display 1300 can also present other information, such as menu screens and/or other images. In the same or a different embodiment, switch mechanism 1600 can also be used to toggle display 1300 to and from presenting such other information. In a different embodiment, switch mechanism 1600 can comprise more than one switch, where different switches can be correlated to additional displays similar to display 1300, and/or to individual transducer arrays similar to transducer arrays 1210 and 1220.

FIG. 1. illustrates power source 1700. In the present embodiment, power source 1700 comprises a portable battery, which can be rechargeable. Power source 1700 is coupled to housing 2500, and is configured to power electrical systems of monitoring device 1000, such as processor 1100 and transducer 1200, among others. In the present embodiment, power source 1700 is located within housing 2500. In a different embodiment, power source 1700 can be attached to an exterior surface of housing 2500. In a different embodiment, power source 1700 can comprise a power cord to recharge power source 1700, where the power cord can be detachable in some examples.

In some embodiments, power source 1700 can be configured to be charged via a docking station (not shown), where the docking station can be tailored accommodate and/or support a portion of the surface of housing 2500. In one embodiment, power source 1700 comprises charging leads 1711-1712 accessible through the exterior of housing 2500, and the docking station comprises contact leads (not shown) complementary with charging leads 1711-1712. The contact leads in the same embodiment can be configured to contact charging leads 1711-1712 to charge power source 1700 when monitoring device 1000 is docked with the docking station. In a different embodiment, the docking station can be configured to charge power source 1700 via one of a capacitive coupling or an inductive coupling, where direct contact between charging and/or contact leads may not be needed.

As shown in FIG. 1, the present embodiment also comprises port 1900 coupled to processor 1100. Port 1900 can be used to place monitoring device 1000 in communication with other electronic devices. For example, port 1900 can be used to interface monitoring device 1000 with a personal computer or a database to transmit information such as scanned images. In one example, port 1900 can comprise a wired port, such as a USB or Firewire® port. In the same or a different example, port 1900 can also comprise a wireless port. In some examples, the docking station described above for power source 1700 can also be configured to couple with port 1900 to facilitate the communication with other electronic devices when monitoring device 1000 is docked with the docking station.

As more clearly illustrated in FIG. 2, monitoring device 1000 comprises a central pointer 2400 configured to indicate a center of an image shown on display 1300. In some embodiments, central pointer 2400 comprises one or more of pointer 2410 on housing 2500, pointer 2420 presented on display 1300, pointer line 2430 presented also on display 1300, and/or pointer 2440 proximate to scanning surface 2250. In the present example, central pointer 2400 indicates a midpoint of display 1300. Central pointer 2400 is correlated to a centerline of transducer array 1210 (FIGS. 1, 3, and 4) in the current example. In the present or a different example, monitoring device 1000 can comprise central pointer 2600, similar to central pointer 2400, but correlated instead to a centerline of transducer array 1220 (FIGS. 1, 3, and 4). In the present embodiment, the centerlines of transducer arrays 1210 and 1220 can correspond to axes 3210 and 3220, respectively, in FIG. 3.

In the present embodiment, housing 2500 comprises gridmarks 2700 aligned along an axis substantially parallel to axis 3220. In addition, monitoring device 1000 comprises grid pointers 2800 configured to demarcate on display 1300 subdivisions correlated to gridmarks 2700. Grid pointers 2800 can comprise physical and/or electronic grid pointers.

As seen in FIG. 3, monitoring device 1000 comprises needle guide 3500 aligned with transducer array 1210 and proximate to a central portion of transducer array 1220. In the present example, needle guide 3500 is coupled to housing 2500 proximate to scanning surface 2250. Needle guide 3500 is substantially in-line with axis 3210 in the present example, and comprises needle alignment groove 3510. In one embodiment, needle guide 3500 can be used to assist a user in aligning a needle with central pointer 2400 prior to and during cannulation of a vascular vessel presented on display 1300.

Figure 7:
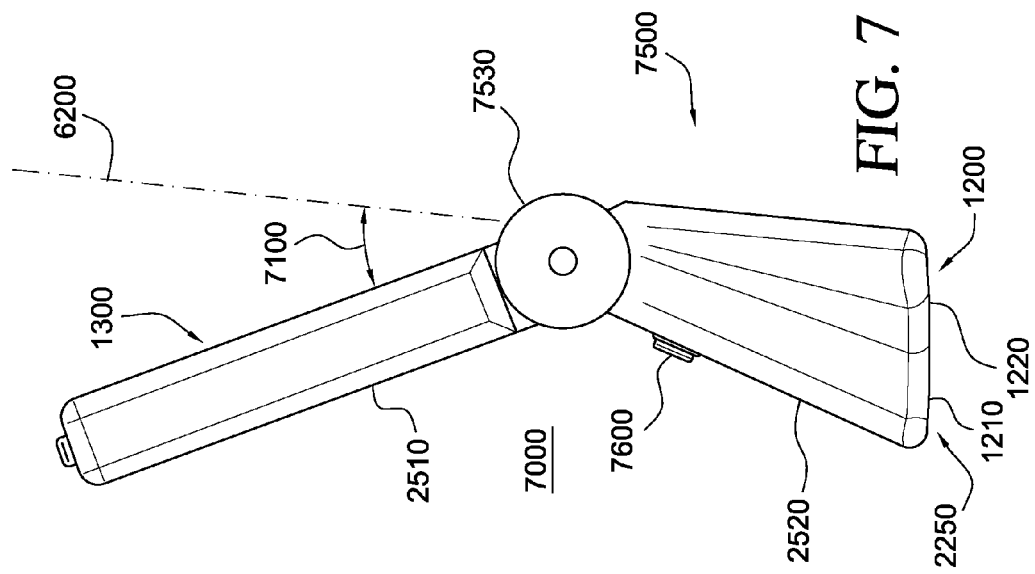
FIG. 7 illustrates a side view of a different monitoring device.
Figure 6:
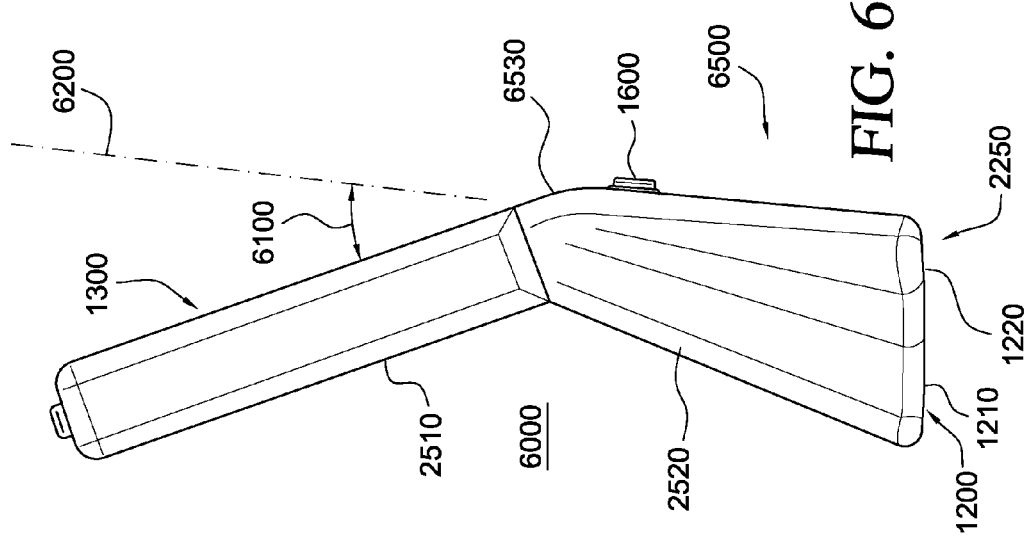
FIG. 6 illustrates a side view of another monitoring device.

Continuing with the figures, FIG. 6 illustrates a side view of monitoring device 6000. FIG. 7 illustrates a side view of monitoring device 7000.

Monitoring devices 6000 and 7000 are similar to monitoring device 1000 (FIGS. 1-6), but differ by comprising housings 6500 and 7500, respectively, similar to housing 2500 (FIG. 2). Housing 6500 in FIG. 6 comprises joint 6530 between portions 2510 and 2520 of housing 6500. Similarly, housing 7500 in FIG. 7 comprises joint 7530 between portions 2510 and 2520 of housing 7500. In contrast with joint 2530 of housing 2500 (FIG. 2), where portions 2510 and 2520 of housing 2500 are substantially planar relative to each other, joints 6530 and 7530 permit their respective portions 2510 and 2520 to be angled relative to each other to facilitate viewing of display 1300.

FIG. 6 shows portion 2510 is fixedly angled towards a rear of monitoring device 6000 at angle 6100. In the present example, angle 6100 comprises approximately 25 degrees. In some examples, angle 6100 can be fixed at approximately between 10 to 45 degrees. In the example of FIG. 7, joint 7530 permits portion 2510 to be variably angled and adjustable relative to portion 2520 of housing 7500. In some embodiments, angle 7100 can be varied between approximately 0 and 90 degrees. In some examples, display 1300 can also be rotated about axis 6200.

In the example of FIG. 7, monitoring device 7000 comprises switch mechanism 7600, similar to switch mechanism 1600 of FIGS. 1-3 and 6. Switch mechanism 7600 differs by being located towards the rear of monitoring device 7000 such as to be operable in a pistol-trigger fashion. This arrangement could facilitate the single-handed operation of monitoring device 7000 when portion 2520 of housing 7500 is grabbed by a hand.

Figure 8:
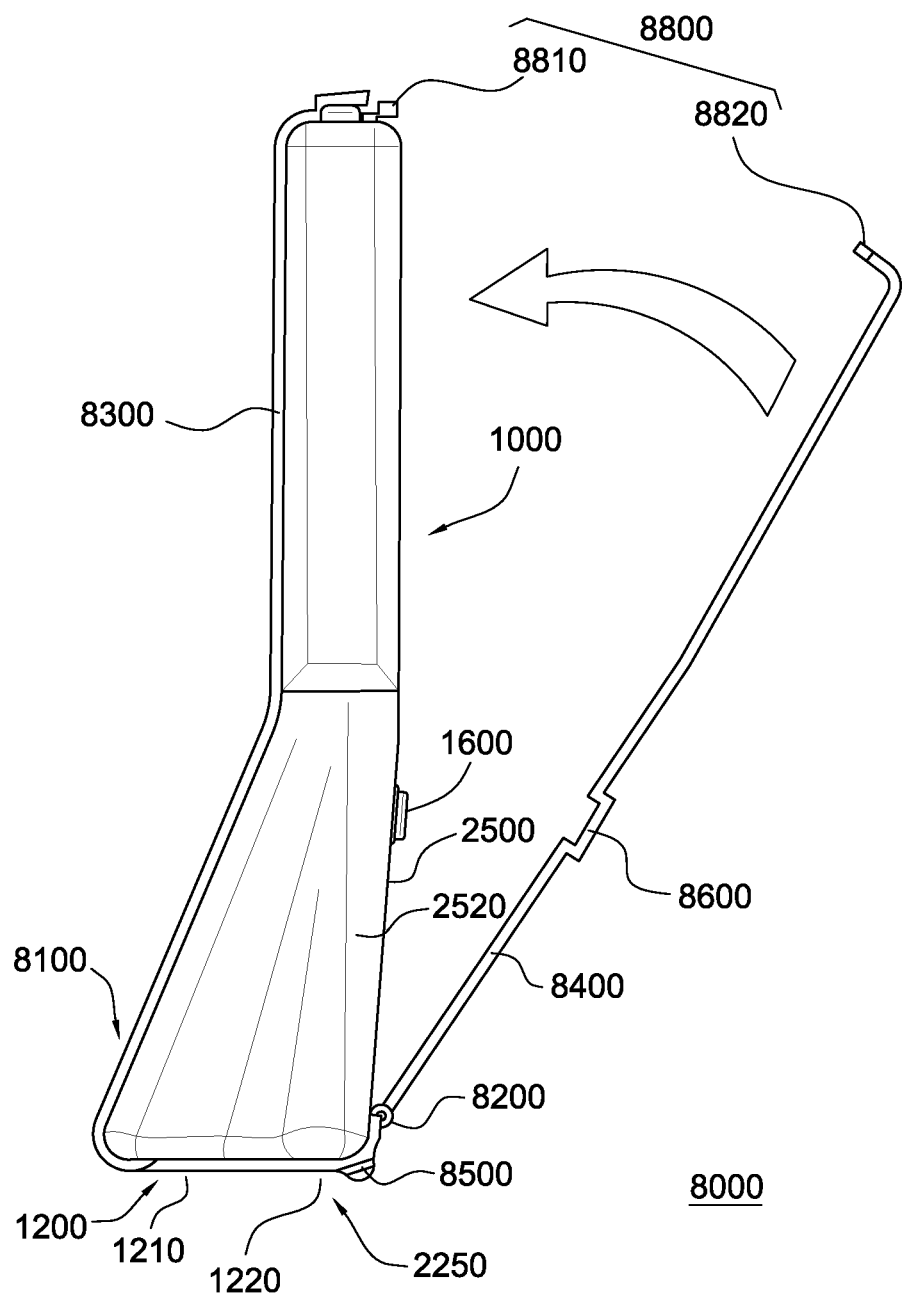
FIG. 8 illustrates a side view of the monitoring device of FIG. 1 partially covered by a casing.
Figure 10:
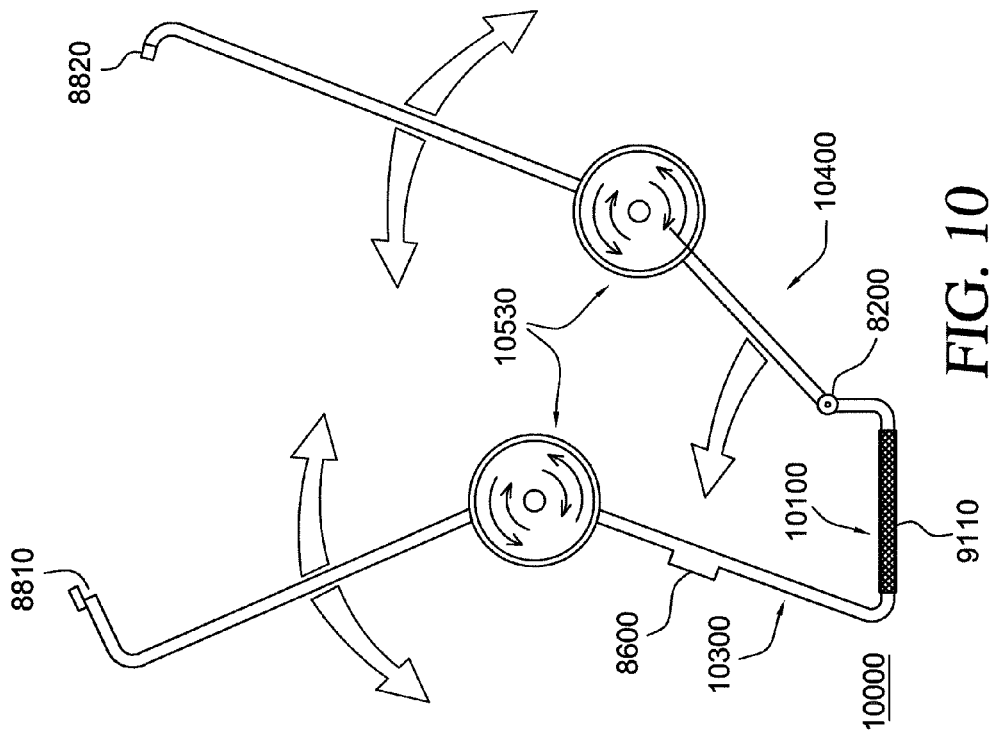
FIG. 10 illustrates a cross-sectional side view of a different casing configured to cover the monitoring device of FIG. 7.
Figure 9:
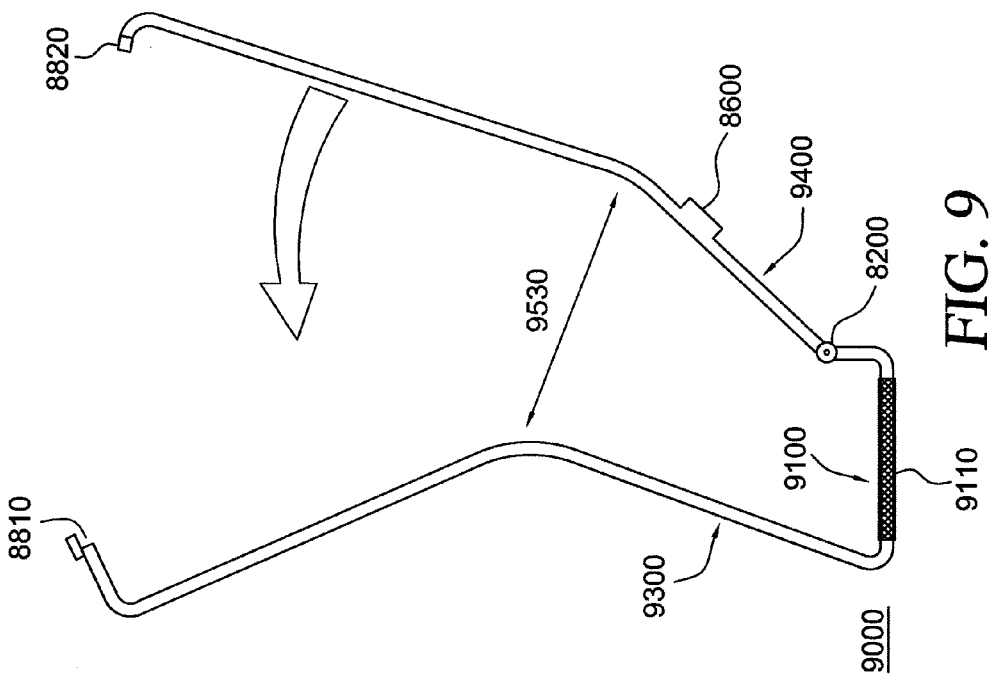
FIG. 9 illustrates a cross-sectional side view of another casing configured to cover the monitoring device of FIG. 6.

Moving on, FIG. 8 illustrates a side view of monitoring device 1000 (FIGS. 1-5) partially covered by casing 8000. FIG. 9 illustrates a cross-sectional side view of casing 9000 configured to cover monitoring device 6000 (FIG. 6). FIG. 10 illustrates a cross-sectional side view of casing 10000 configured to cover monitoring device 7000 (FIG. 7). In some embodiments, at least one of casings 8000, 9000, and/or 10000 can be referred to as a cover.

Casing 8000 comprises transducer cover portion 8100, configured to removably envelop at least a portion of housing 2500. In the present embodiment, transducer arrays 1210 and 1220 are arranged in a T-shape, as shown in FIG. 4, and portion 8100 is configured to accommodate the T-shape. Casing 8000 comprises hinge 8200 to permit portions 8300 and 8400 to envelop monitoring device 1000 in a clamshell fashion. Transducer cover portion 8100 is transparent proximate to scanning surface 2250 with respect to transducer arrays 1210 and 1220 such as to minimize interference with the transmission and reception of signals from transducer 1200.

In the present example, transducer cover portion 8100 also comprises needle guide 8500, similar to needle guide 3500 as described above for FIG. 3. Casing 8000 is configured to be disposable and/or sterilizable, such that monitoring device 1000 can be brought into and used at a clean room or sterile environment.

Casings 9000 and 10000 are similar to casing 8000, but differ by allowing for an angle between portions 2510 and 2520 of monitoring devices 6000 and 7000. Similar to casing 8000, casings 9000 and 10000 also comprise hinge 8200 to permit portions 9300 and 9400, and portions 10300 and 10400, respectively, to envelop monitoring devices 6000 and 7000 in a clamshell fashion. In the embodiments of FIGS. 8-10, locks 8810 and 8820 of locking mechanism 8800 can be brought together to secure casings 8000, 9000, and 10000 when closed.

In some embodiments, one or more portions of casings 8000, 9000, and/or 10000 can comprise materials such as rigid plastic, semi-rigid plastic, and/or flexible materials such as silicone. In the same or a different embodiment, at least a portion of casings 8000, 9000, and/or 10000 can conform to a shape of a portion of monitoring device 1000, 6000, and/or 7000. As an example, portion 9530 of casing 9000 in FIG. 9 and portion 10530 of casing 10000 in FIG. 10 can comprise a semi-rigid or flexible material to accommodate the envelopment of joint 6530 (FIG. 6) or joint 7530 (FIG. 7). In the same or a different embodiment, portion 9530 of casing 9000 and portion 10530 of casing 10000 can be configured in an accordion manner to allow for the angle between portions 2510 and 2520. In some embodiments, switch mechanisms 1600 (FIGS. 1, 6, 8) and 7600 (FIG. 7) of respective monitoring devices 1000, 6000, and 7000 can be covered by pliable portions 8600 of casings 8000, 9000, and 10000, respectively. In some examples, pliable portions 8600 can comprise materials similar to those materials described above for portion 9530, and can permit a user to operate switch mechanisms 1600 and 6600 while covered by casings 8000, 9000, and 10000.

The embodiments shown in FIGS. 9-10 show transducer casings 9100 and 10100 comprising gel-pack 9110 positioned proximate to transducer arrays 1210 and 1220 (FIGS. 6-7). In some embodiments, gel-pack 9110 can comprise a bladder filled with an aqueous, flexible gel material suitable for the transmission of ultrasound signals. In the same or a different embodiment, gel-pack 9110 can be similar to an Aquaflex® gel pad from Parker Laboratories, Inc. In a different embodiment, casing 8000 can also comprise gel-pack 9110.

In some embodiments, part of transducer cover portion 8100 can comprise a non-stick material proximate to scanning surface 2250 to facilitate sliding monitoring device 1000 over a target surface. In the same or a different embodiment, one or more of transducer cover portions 8100, 9100, and/or 10100 can comprise a T-shape tailored to dimensions of transducer arrays 1210 and 1220 on portion 2520 (FIGS. 3-4). In the some examples, a thickness of a portion of one or more of casings 8000, 9000, and/or 10000 comprises approximately between 0.5 to 5 millimeters. In a embodiment different than as illustrated in FIGS. 8-10, a cover similar to casing 8000 can be configured to leave display 1300 exposed so as to cover only, for example, portion 2520 of monitoring device 1000.

In some embodiments, monitoring devices 6000 and 7000 can be charged via a docking station (not shown), similar to as described above for monitoring device 1000. In the same or a different example, the docking station can also be configured to charge power source 1700 while monitoring devices 1000, 6000, and/or 7000 are covered by casings 8000, 9000, and 10000, respectively.

Figure 11:
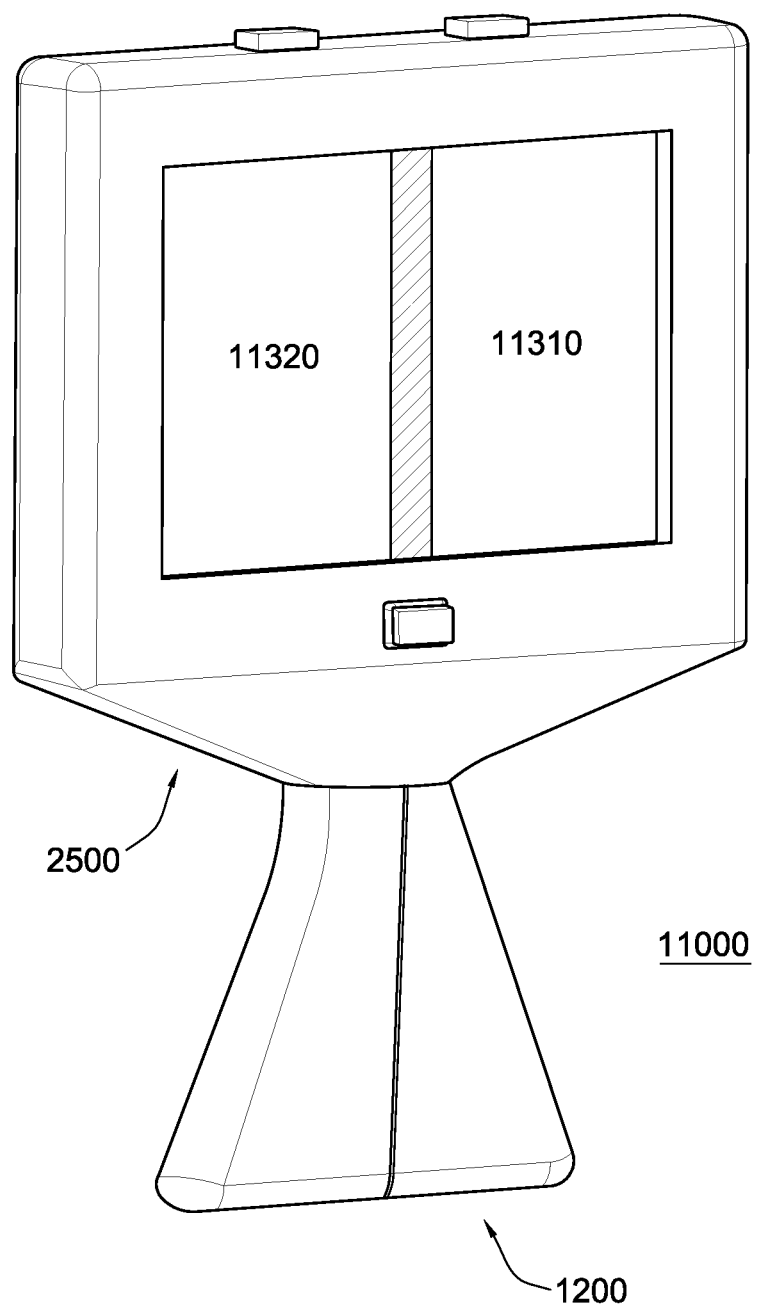
FIG. 11 illustrates a perspective view of yet another monitoring device.
Figure 12:
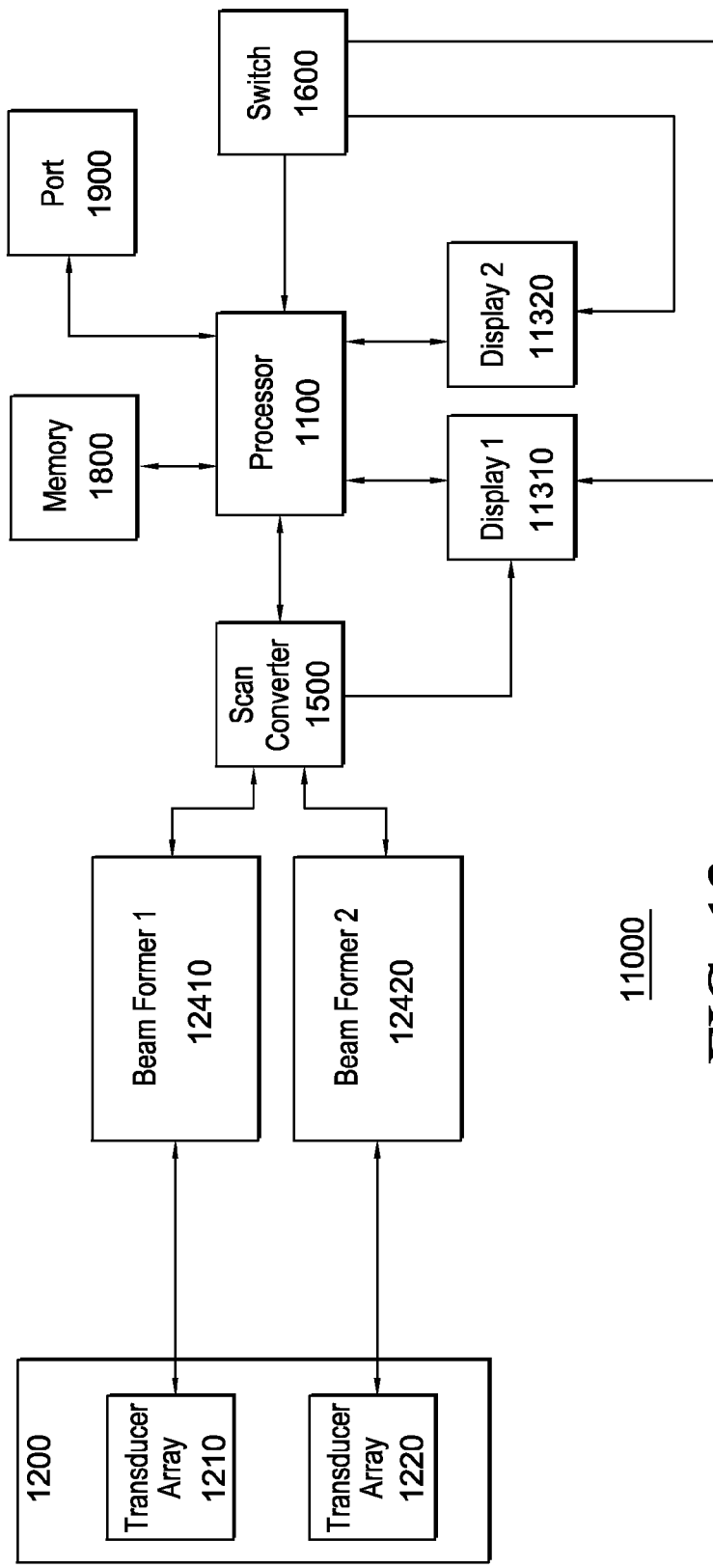
FIG. 12 illustrates a block diagram of the monitoring device of FIG. 11.

Continuing with the figures, FIG. 11 illustrates a perspective view of a monitoring device 11000. FIG. 12 illustrates a block diagram of monitoring device 11000. Monitoring device 11000 is similar to monitoring device 1000, but comprises displays 11310 and 11320 rather than a single display. In the same or other examples, displays 11310 and 11320 can comprise different portions of a common screen. Monitoring device 11000 comprises transducer 1200 like monitoring device 1000, and is configured to simultaneously present images correlated to readings from transducer array 1210 on display 11310, and images correlated to readings from transducer array 1220 on display 11320. As seen in FIG. 12, monitoring device 11000 comprises beamformers 12410 and 12420 configured to control and couple to transducer arrays 1210 and 1220, respectively. In the present embodiment, beamformers 12410 and 12420 connect to scan converter 1500, although in a different embodiment beamformers 12410 and 12420 can connect to their own dedicated scan converters.

Figure 14:
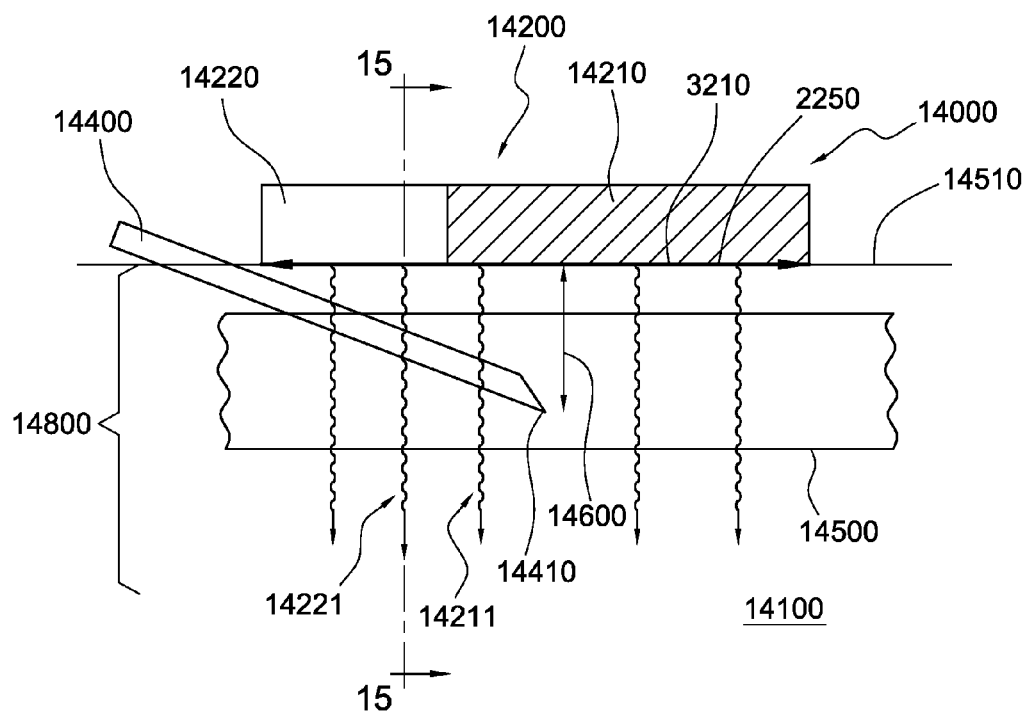
FIG. 14 illustrates a longitudinal cross-section of a target zone during cannulation of a blood vessel by a needle, as monitored by a monitoring device similar to those of the figures above.
Figure 15:
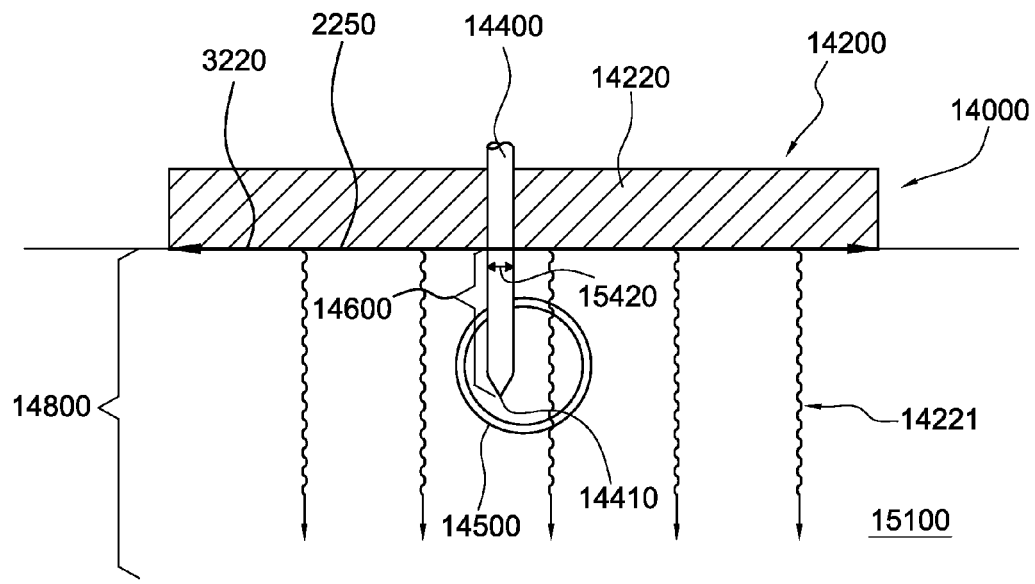
FIG. 15 illustrates a transverse cross-section of the target zone of FIG. 14.

Skipping ahead in the figures, FIG. 14 illustrates a longitudinal cross-section of target zone 14800 during cannulation of blood vessel 14500 by needle 14400, as monitored by monitoring device 14000. FIG. 15 illustrates a transverse cross-section of target zone 14800 during the cannulation of blood vessel 14500. FIGS. 14-15 are related in that FIG. 15 presents transverse plane 15100 of target zone 14800 along line 15-15 of FIG. 14, while FIG. 14 presents longitudinal plane 14100 of target zone 14800. For simplicity, only transducer 14200 of monitoring device 14000 is shown in FIGS. 14-15, but monitoring device 14000 can be similar to one of monitoring devices 1000 (FIGS. 1-3, 8), 6000 (FIG. 6), 7000 (FIG. 7), or 11000 (FIG. 11).

Figure 16:
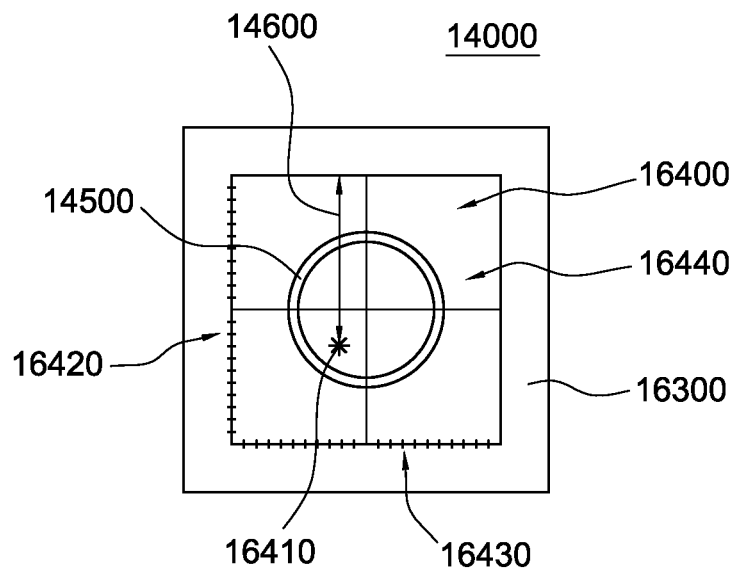
FIG. 16 illustrates an image of a transverse view of the cannulation of FIGS. 14-15 as presented on a display of the monitoring device of FIG. 14.
Figure 17:
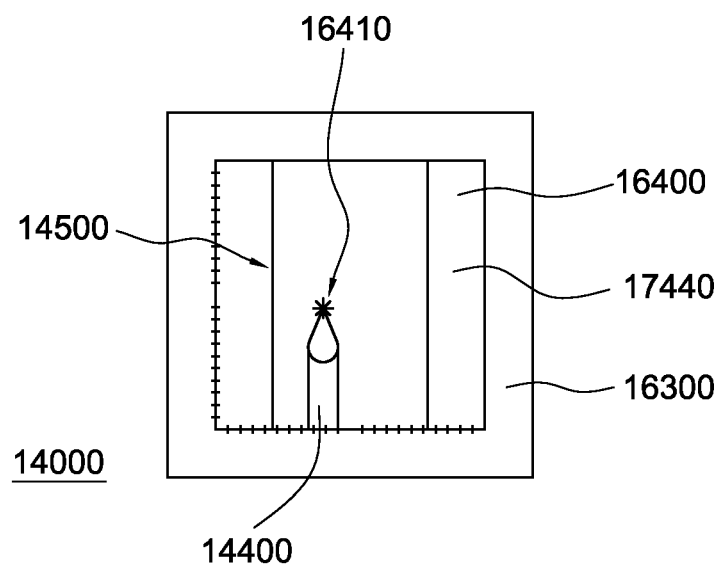
FIG. 17 illustrates an image of a longitudinal view of the cannulation of FIGS. 14-15 as presented on the display of the monitoring device of FIG. 14.

In the present example transducer 14200 is located over target zone 14800, and comprises transducer array 14210 aligned longitudinally with respect to blood vessel 14500 for longitudinal scan 14211 of the longitudinal cross-section of FIG. 14 along axis 3210 (FIG. 14) of scanning surface 2250. Similarly, transducer array 14220 can be aligned transversely with respect to blood vessel 14500 for transverse scan 14221 of the transverse cross-section of FIG. 15 along axis 3220 (FIG. 15) of scanning surface 2250. In some examples, transducer array 14210 can be similar to transducer array 1210 of transducer 1200 (FIG. 4), and/or to transducer array 5210 of transducer 5200 (FIG. 5). In the same or other examples, transducer array 14220 can be similar to transducer array 1220 of transducer 1200 (FIG. 4), and/or of transducer 5200 (FIG. 5). FIG. 16 illustrates image 16400 of transverse view 16440 of the cannulation of blood vessel 14500 of FIGS. 14-15. FIG. 17 illustrates image 16400 of longitudinal view 17440 of the cannulation of blood vessel 14500 of FIGS. 14-15. Image 16400 is presented on display 16300, which can be similar to display 1300 of monitoring device 1000 (FIG. 1) and/or to one or both of displays 11310 and 11320 of monitoring device 11000 (FIG. 11).

In the present example, needle 14400 is introduced into skin surface 14510 and routed until needle 14400 cannulates blood vessel 14500. The routing of needle 14400 is monitored by monitoring device 14000, which is placed over skin surface 14510 above blood vessel 14500, so that transducer 14200 can subdermally scan the progress of needle 14400 towards blood vessel 14400. Display 16300 is configured to present image 16400, where image 16400 can comprise transverse view 16440 of the transverse cross-section of FIG. 15 along axis 3220 to illustrate the progress of needle 14400. In FIG. 16, display 16300 is also configured to present, at image 16400, needle point highlight 16410 of needle point 14410 (FIG. 14). Needle point highlight 16410 can be used to represent needle point depth 14600 (FIGS. 14 & 16), comprising a distance from transducer 14200 at skin surface 14510 to needle point 14410, as measured by transducer array 14210 along the longitudinal cross-section of FIG. 14.

Although image 16400 is based primarily on transverse scan 14221 of target zone 14800 by transducer array 14220 (FIG. 15), display 16300 also can be configured to locate needle point highlight 16410 at image 16400, based on needle point depth 14600, as detected by transducer 14210 (FIG. 14) via longitudinal scan 14211 of target zone 14800. As a result, even though needle point 14410 is past the range of transverse scan 14221, data from longitudinal scan 14211 can be used to present needle point highlight 16410 at image 16400 in FIG. 17. In the present example, needle point 14410 is located at a tip or end of needle 14400, but there may be other examples where needle point 14410 may represent another point along a length of needle 14400. In some examples, needle point highlight 16410 can comprise a graphic of a dot, where the dot may be white or colored, solid or hollow, and/or constant or blinking. The dot also may comprise one or more geometric shapes, such as oval, triangle, or square, among others.

Monitoring device 14000 of FIGS. 14-16 can comprise architectures similar to those presented in FIGS. 1 and/or 12. In the present example, processor 1100 (FIG. 1) of monitoring device 14000 is configured to receive and process data from transducer 14210 about longitudinal scan 14211 to determine needle point depth 14600. Processor 1100 also is configured to instruct display 16300 to locate needle point highlight 16410 at a longitudinal coordinate 16420 (FIG. 16) of display 16300, where longitudinal coordinate 16420 corresponds to a position in display 16300 representative of the needle point depth. In the example of FIG. 16, longitudinal coordinate 16420 corresponds to a coordinate of a y-axis of display 16300.

In some examples, at least one of transducers 14210 or 14220 can be configured to detect a location of needle width 15420 along the transverse cross-section of FIG. 15. There can be examples where needle width 15420 is detected by transducer array 14220 via transverse scan 14221. Needle width 15420 may also be detected by transducer array 14210 via longitudinal scan 14211 in the same or other examples. Data concerning the detection of needle width 15420 can be received and processed by processor 1100, which can instruct display 16300 to locate needle point highlight 16410 at transverse coordinate 16430 corresponding to a position in display 16300 representative of the location of needle width 15420. In the example of FIG. 16, longitudinal coordinate 16430 corresponds to a coordinate of an x-axis of display 16300. In the same or other examples, longitudinal coordinate 16420 and/or transverse coordinate 16430 may correspond to coordinates of one or more pixels of display 16300.

As described above, monitoring device 14000 can be similar to the other monitoring devices described herein, and can share similar features. For example, monitoring device 14000 can comprise switch 1600. In the present example, display 16300 can be configured such that, when switch 1600 (FIG. 1) is at the first setting, image 16400 presents a longitudinal view of the longitudinal cross-section of target zone 14800, as derived from longitudinal scan 14211 by transducer array 14210 and as shown in FIG. 17. Similarly, display 16300 can be configured such that, when switch 1600 is at the second setting, image 16400 presents transverse view 16440 of the transverse cross-section of target zone 14800, as shown in FIG. 16 and as derived from transverse scan 14221 by transducer array 14220 with needle point highlight 16410, as derived from longitudinal scan 14211 by transducer array 14210.

In some embodiments, monitoring device 14000 can be configured such that transducer array 14210 is operable at a first frequency, while transducer array 14220 is operable at a second frequency. In the same or other examples, the first and second frequencies can be configured to be substantially non-interfering with each other, such that transducer arrays 14210 and 14220 may be operated simultaneously to concurrently present and update transverse view 16440 and needle point highlight 16410 without disturbing longitudinal scan 14211 and/or transverse scan 14221. Although the first and second frequencies can be different from each other, there can be examples where the first and second frequencies can be the same if they are substantially non-interfering with each other during operation of transducer arrays 14210 and 14220.

There also can be embodiments where monitoring device 14000 can be configured such that transducer arrays 14210 and 14220 are alternatingly oscillatable relative to each other to permit concurrent presentation of transverse view 16440 and needle point highlight 16410 at image 16400. As an example, transducer arrays 14210 and 14220 can be alternatingly oscillated at a high rate such that, when transducer array 14210 is activated to perform longitudinal scan 14211, transducer array 14220 is deactivated to cease transverse scan 14221. Similarly, when transducer array 14220 is activated for transverse scan 14221, transducer array 14220 is deactivated to cease longitudinal scan 14211.

In some embodiments, a monitoring device similar to one or more of monitoring devices 1000 (FIGS. 1-3, 8), 6000 (FIG. 6), 7000 (FIG. 7), 11000 (FIG. 11), or 14000 (FIGS. 14-17) may be configured to track and/or direct a probe or catheter as the probe is routed along a vessel such as blood vessel 14500 (FIGS. 14-15). In some examples, the probe may comprise a needle and/or a catheter such as a peripherally inserted central catheter (PICC catheter). The probe may be monitored and inserted into the vessel as described in FIGS. 14-17 for needle 14400, and may be then routed to a desired location along the vessel with further aid from the monitoring device. For example, the monitoring device may be moved over the skin surface and along the vessel to monitor the progress of the probe as it makes its way through the vessel. In the same or other examples, the probe may comprise a sensor, and the monitoring device may be configured to process signals received from the sensor of the probe. The sensor of the probe can be located at one or more locations, such as at a tip of the probe, and/or along a length of the probe. In the same or other examples, the sensor may comprise a wire lead, and/or a column of saline. For instance, the sensor of the probe may be configured to detect a proximity signal, such as a change in P-waves of an electrocardiogram (EKG) as the tip of the probe approaches a desired location along the vessel proximate to the atria of the heart. In this example, the monitoring device can be configured to recognize when the sensor of the probe detects the proximity signal to indicate that the probe has reached the desired location. In some examples, the monitoring device can react to the signals from the sensor of the probe by actuating a proximity indicator to indicate that the probe is at or proximate to the desired location. In some examples, the proximity indicator may emit a visual indication and/or an auditory indication. The visual indication may be presented at a display of the monitoring device, such as display 16300 (FIG. 16), and/or by blinking a light such as a light emitting diode (LED).

Other sensors may be placed elsewhere on a patient's body to monitor the probe's approach to the desired location together with the sensor of the probe. There can be examples where the sensor of the probe and/or the other sensors described above may couple to an accessory box configured to process information from such sensors and to communicate with the monitoring device to actuate the proximity indicator. In the same or other embodiments, the monitoring device may communicate wirelessly to receive information from the sensor of the probe, from the other sensors, and/or form the accessory box.

Figure 19:
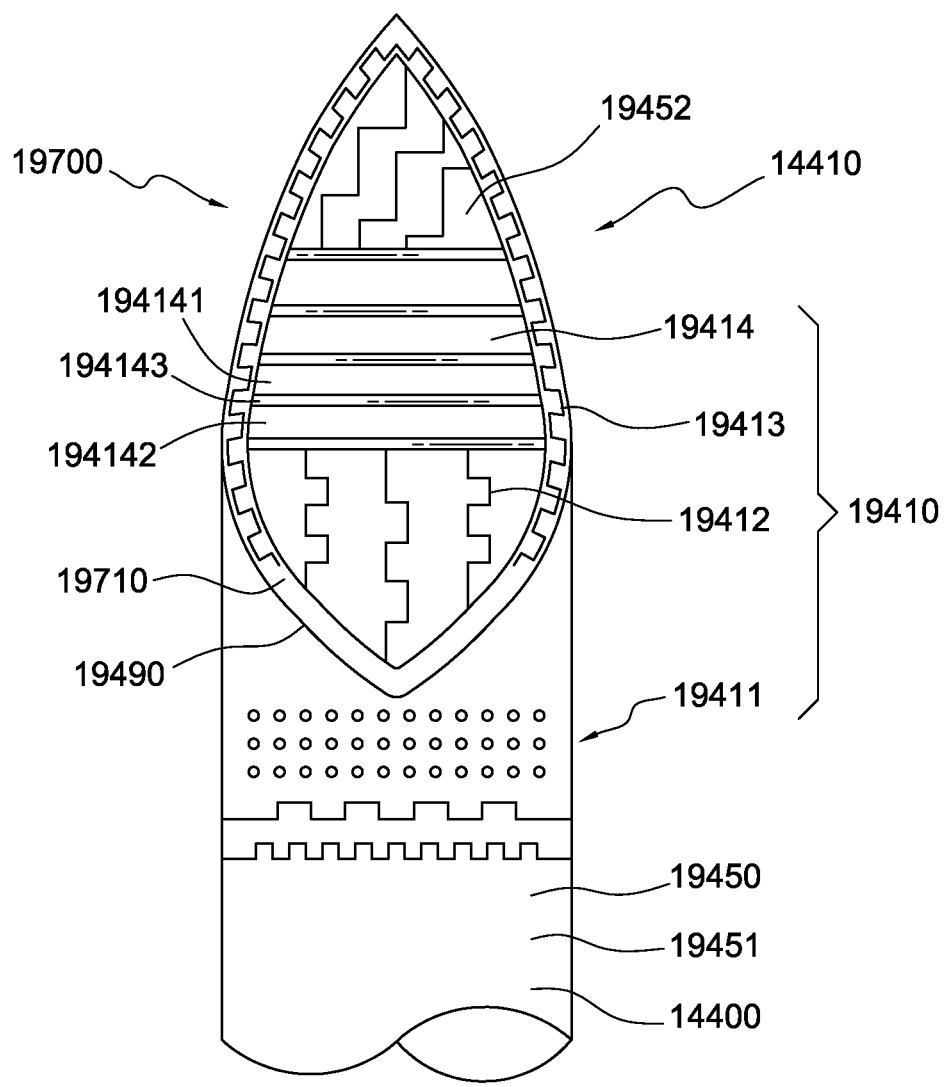
FIG. 19 illustrates a top view of a tip of the needle of FIG. 14.
Figure 20:
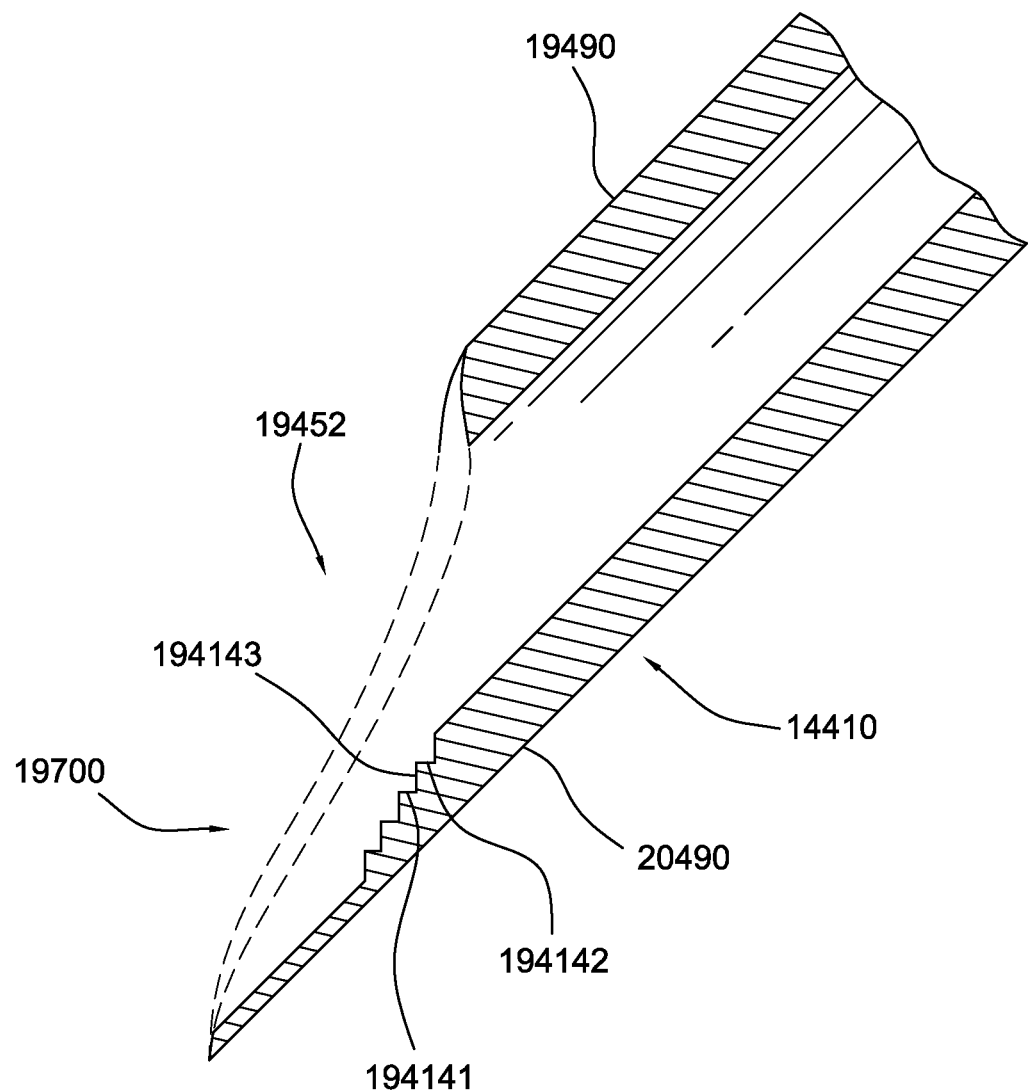
FIG. 20 illustrates a cross-sectional side view of the tip of FIG. 19.

Continuing with the figures, FIG. 19 illustrates a top view of tip 14410 of needle 14400. FIG. 20 illustrates a cross-sectional side view of tip 14410 of needle 14400.

Needle 14400 comprises shaft 19450 with interior surface 19452 and exterior surface 19451. Needle 14400 also comprises bevel 19700 of needle tip 14410, where bevel 19700 is shaped to ease the insertion of needle 14400 during cannulation of target zone 14800 (FIG. 14). In the present example, needle 14400 also comprises one or more indentations 19410, such as indentations 19411-19414, configured to enhance ultrasonic beam reflections proximate to needle tip 14410. As can be seen in FIG. 14, needle 14400 is inserted "bevel-up" into target zone 14800 so that bevel edge thickness 19710, interior surface 19452, and/or indentations 19410 can enhance reflection and echotexture proximate to bevel 19700 for transducer 14200. There also can be examples where one or more or more portions proximate to needle tip 14410, such as bevel edge thickness 19710, can be flared for further enhanced reflection.

In the present example, indentation 19412 comprises a groove located on interior surface 19452 at bevel 19700. Indentation 19413 comprises a groove located at bevel edge thickness 19710 of bevel 19700, where bevel edge thickness 19710 extends between interior surface 19452 and exterior surface 19451 of shaft 19450. Indentations 19411 are located proximate to needle tip 14410 on exterior surface 19451. In some examples, indentations 19411 can be located on exterior surface 19451 along a needle spine region, where the needle spine region is located along an apex of the needle when the needle is "bevel-up." Several patterns can be seen for indentations 19410 in FIG. 19, including stairstep groove patterns, square function groove patterns, and geometric figured patterns, among others.

The present example also encompasses indentation 19414, comprising a stair structure at interior surface 19452, with ledge 194141 at a lower level of interior surface 19452, ledge 194142 at an upper level of interior surface 19452, and riser 194143 coupled between ledges 194141-194142. As can be seen in FIG. 20, interior surface 19452 at bevel 19700 is visible from top side 19490 of needle 14400, and bottom side 20490 of needle 14400 is opposite top side 19490. Ledges 194141-194142 are configured such that the lower level of ledge 194141 is closer to bottom side 20490 than the upper level of ledge 194142.

The location of indentations 19410 as described above can be beneficial, for example, to enhance ultrasonic beam reflections as close as possible to the end of needle tip 14410 for better localization thereof by monitoring device 14000 (FIG. 14), and/or by other ultrasound monitoring devices. In some examples, interior surface 19452 at bevel 19700 may be at least partially flattened to better direct ultrasonic beam reflections therefrom. For example, ledges 194141-194142 can be substantially flat, and can be set at an angle to reflect ultrasonic beams more directly towards a monitoring device, such as monitoring device 14000 (FIGS. 14-17). With respect to the illustration of FIG. 14, ledges 194141-194142 can be angled, relative to a length of needle 14400, to be substantially parallel to transducer 14200 when needle 14400 is inserted into target zone 14800. There also can be examples where a stair structure similar to that of indentation 19414 can be located elsewhere, such as at bevel edge thickness 19710 and/or at the needle spine of needle 14400. Although FIG. 19 illustrates several different kinds of indentations 19410, other examples may comprise only one type of indentation pattern rather than the combination shown for FIGS. 19-20.

Figure 13:
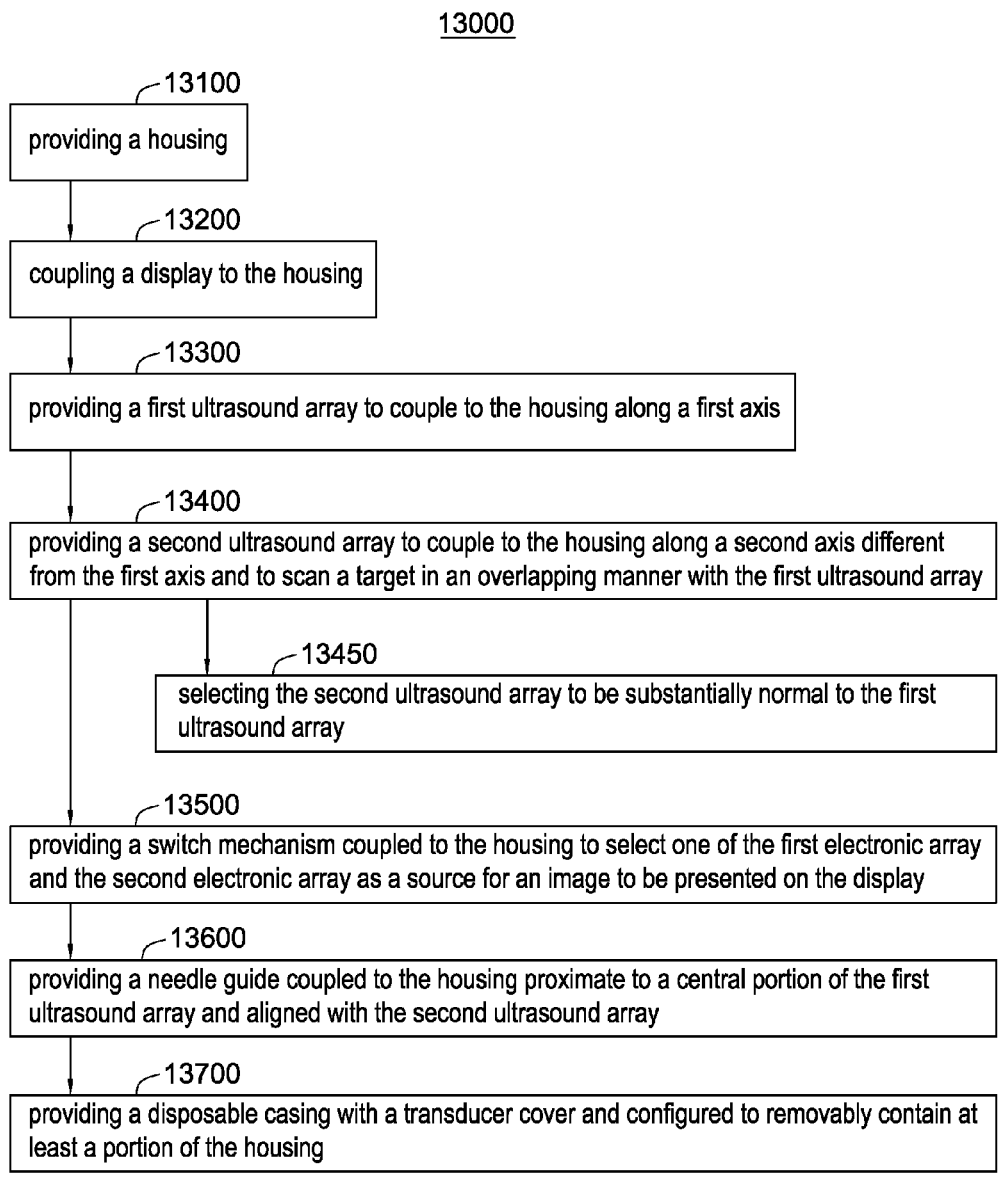
FIG. 13 illustrates a block diagram of a method of manufacturing a handheld imaging device similar to the monitoring devices of FIGS. 1-11.

Backtracking through the figures, FIG. 13 illustrates a block diagram of method 13000 for manufacturing a handheld imaging device. In some embodiments, the handheld imaging device can be one of monitoring devices 1000 (FIGS. 1-3, 8), 6000 (FIG. 6), 7000 (FIG. 7), 11000 (FIGS. 11-12), and 14000 (FIGS. 14-16).

Block 13100 of method 13000 comprises providing a housing. In one example, the housing can be one of housings 2500 (FIGS. 2, 3, 8, 11), 6500 (FIG. 6), 7500 (FIG. 7), or the housing for monitoring device 14000 (FIGS. 14-17).

Block 13200 of method 13000 comprises coupling a display to the housing of block 13100. In some examples, the display can be similar to the display described above for display 1300 (FIGS. 1-2), 11310, 11320 (FIGS. 11-12), and/or 16300 (FIG. 16).

Block 13300 of method 13000 comprises providing a first ultrasound array to couple to the housing of block 13100 along a first axis. In some examples, the first ultrasound array can be similar to the array described above for transducer arrays 1210 (FIGS. 1, 3, 4), 5210 (FIG. 5), and/or 14210 (FIG. 14). For example, the first transducer array can be aligned to scan a longitudinal plane of a target subdermal region, as illustrated in FIG. 14 for transducer array 14210 with respect to longitudinal plane 14100 and target zone 14800. Similarly, the first axis can be similar to axis 3210 in FIGS. 3 and 14.

Block 13400 of method 13000 comprises providing a second ultrasound array to couple to the housing of block 13100 along a second axis different from the first axis of block 13300, and to scan a target in an overlapping manner with the first ultrasound array of block 13300. In one embodiment, the second ultrasound array can be similar to the array described above for transducer array 1220 (FIGS. 1, 3, 4, 5), and/or 14220 (FIGS. 14-15). For example, the second transducer array can be aligned to scan a transverse plane of a target subdermal region, as illustrated in FIG. 15 for transducer array 14220 with respect to transverse plane 15100 and target zone 14800. Similarly, the second axis can be similar to axis 3220 in FIGS. 3 and 15.

In one embodiment, the first and second ultrasound arrays of blocks 13300 and 13400 can scan the target in an overlapping manner by overlapping as shown and described for transducer arrays 1210 and 1220 in FIG. 4. In a different embodiment, the first and second ultrasound arrays can scan the target in overlapping manner as shown and described for transducer arrays 5210 and 1220 in FIG. 5. There can also be other embodiments where blocks 13300 and/or 13400 may be modified such that the first and second arrays need not scan in an overlapping manner.

Figure 18:
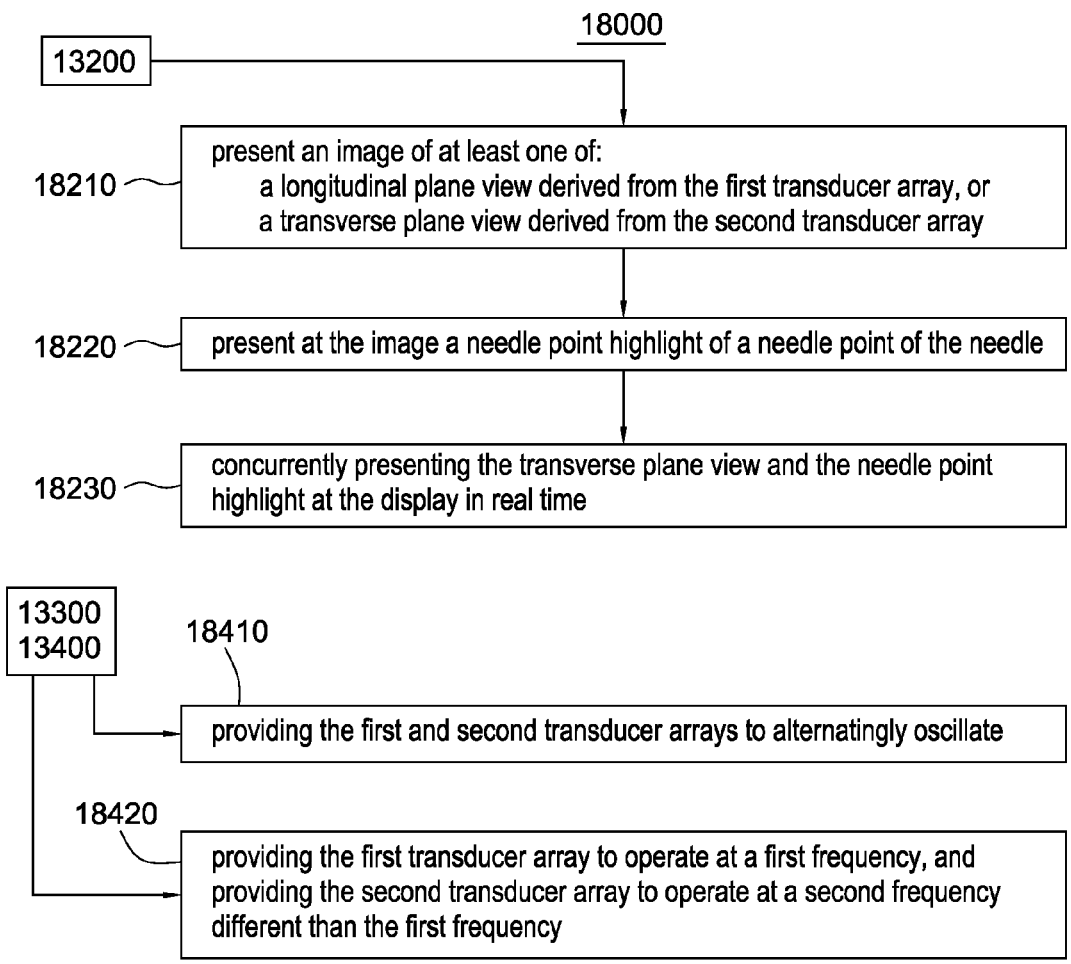
FIG. 18 illustrates a block diagram of an optional flow for blocks 13200, 13300, and 13400 of method 13000.

Skipping ahead in the figures, FIG. 18 illustrates a block diagram 18000 of an optional flow for blocks 13200, 13300, and 13400 of method 13000 in FIG. 13. In the example of FIG. 18, sub-block 18210 of block 13200 involves providing the display to present an image of at least one of a longitudinal plane view derived from the first transducer array, or of a transverse plane view derived from the second transducer array. In some examples, the longitudinal plane view may be similar to that described above for display 11310 (FIG. 11) as derived from transducer array 1210 (FIG. 4) or transducer array 5210 (FIG. 5), and the transverse plane view may be similar to that described above for display 11320 as derived from transducer array 1220 (FIGS. 4-5). In the same or other examples, the longitudinal plane view may be similar to that described above for display 16300 in FIG. 17, as derived from transducer array 14210 (FIG. 14), and the transverse plane view can be similar to that described above for display 16300 in FIG. 16, as derived from transducer array 14220 (FIGS. 14-15). Sub-block 18220 involves providing the display to present at the image a needle point highlight of a needle point of a needle during cannulation. In some examples, the needle can be similar to one of the needles described above used for subdermal cannulation of, for example, blood vessel 14500 (FIGS. 14-17). The needle point highlight can be similar to needle point highlight 16410 for needle point 14410, as shown with respect to needle 14400 of FIGS. 14-17.

In some embodiments comprising sub-block 18220, providing the display in block 13200 can comprise providing the display to locate the needle at a coordinate of the transverse plane view, the coordinate corresponding to a needle point depth detected by the array of block 13300. In such embodiments, block 13300 can comprise providing the first transducer array to detect the needle point depth measured between the transducer and the needle point along the longitudinal plane. As an example, the coordinate of the transverse plane view can be similar to longitudinal coordinate 16420 of transverse view 16440 in FIG. 16, and the needle point depth can be similar to needle point depth 14600 (FIGS. 14-16) as detected by transducer array 14210 (FIG. 14).

Sub-block 18230 of block 18230 comprises concurrently presenting the transverse plane view and the needle point highlight at the display in real time. In some examples, sub-block 18230 can be enabled by sub-block 18410, comprising providing the first and second transducer arrays in blocks 13300 and 13400 to alternatingly oscillate, such as to prevent or limit interference between respective transverse and longitudinal scans, as described above with respect to transducer arrays 14210 and 14220 for FIGS. 14-17.

There also can be examples where sub-block 18230 can be enabled by sub-block 18420, comprising providing the first transducer array to operate at a first frequency, and providing the second transducer array to operate at a second frequency different than the first frequency, such as to prevent or limit interference between respective transverse and longitudinal scans, as described above with respect to transducer arrays 14210 and 14220 for FIGS. 14-17.

Backtracking to FIG. 13, Block 13450 of method 13000 comprises selecting the second ultrasound array of block 13400 to be substantially normal to the first ultrasound array of block 13300. Block 13450 can be a sub-part of block 13400. In some examples, the second ultrasound array of block 13400 can be substantially normal to the first ultrasound array of block 13300 as shown in FIG. 4 for transducer arrays 1210 and 1220, or as shown in FIG. 5 for transducer arrays 5210 and 1220.

Block 13500 of method 13000 comprises providing a switch mechanism coupled to the housing of block 13100 to select one of the first electronic array of block 13300 and the second electronic array of block 13400 as a source for an image to be presented on the display of block 13200. In one embodiment, the switch mechanism can be similar to switch mechanism 1600 (FIGS. 1-3). In the same or a different example, the switch mechanism can be configured to deactivate the second ultrasound array of block 13400 and activate the first ultrasound array of block 13300 in response to a first setting of the switch mechanism, and to deactivate the first ultrasound array of block 13300 and activate the second ultrasound array of block 13400 in response to a second setting of the switch mechanism. In the same or a different example, the display of block 13200 is configured to present images scanned from the first ultrasound array of block 13300 in response to the first setting of the switch mechanism, and to present images scanned from the second ultrasound array of block 13400 in response to the second setting of the switch mechanism.

Block 13600 of method 13000 comprises providing a needle guide aligned with the first transducer array of block 13300 and proximate to a central portion of the second transducer array of block 13400. In some examples, the needle guide can be similar to the guide described for needle guide 3500 (FIG. 3).

Block 13700 of method 13000 comprises providing a disposable casing with a transducer cover and configured to removably contain at least a portion of the housing of block 13100. In some examples, the disposable casing can be as described above for casings 8000, 9000, and/or 10000 (FIGS. 8-10).

In some embodiments, the sequence of blocks 13100, 13200, 13300, 13400, 13450, 13500, 13600, and/or 13700 of method 13000 can be changed or otherwise altered. For example, sub-blocks 18220 and 18210 of block 13200 can be swapped in sequence. In the same or a different embodiment, one or more of blocks 13100, 13200, 13300, 13400, 13450, 13500, 13600, and/or 13700 of method 13000 can comprise parts of a single block. For example, sub-blocks 18210 and/or 18220 can be sub-parts of sub-block 18230.

Although the disclosure herein has been described with reference to specific embodiments, it will be understood by those skilled in the art that various changes may be made without departing from the spirit or scope of the invention. For example, method 13000 of FIG. 13 can be expanded with further blocks. In one example, method 13000 could further comprise coupling a beamformer, such as beamformer 1400 (FIG. 1), with the first and second ultrasound arrays. In the same or a different example, method 13000 can further comprise coupling a scan converter, such as scan converter 1500 (FIG. 1), with the display of block 13200. In the same or a different example, method 13000 can further comprise incorporating the display of block 13200, and the first and second ultrasound arrays of blocks 13300 and 13400, with the housing of block 13100. In the same or a different example, method 13000 can further comprise providing a portable and/or rechargeable power source, such as power source 1700 (FIG. 1), coupled to the housing of block 13100. In the same or a different example, method 13000 can further comprise configuring the housing of block 13100 for single-handed and/or non-dominant-handed operation of the handheld imaging device, as described above for monitoring device 1000. Such alternate configurations would not depart from the inventive concepts herein disclosed. Additional examples have been given in the foregoing description.

Accordingly, the disclosure of embodiments in the disclosure is intended to be illustrative of the scope of the invention and is not intended to be limiting. It is intended that the scope of the invention shall be limited only to the extent required by the appended claims. To one of ordinary skill in the art, it will be readily apparent that the handheld imaging devices and related methods discussed herein may be implemented in a variety of embodiments, and that the foregoing discussion of certain of these embodiments does not necessarily represent a complete description of all possible embodiments. Rather, the detailed description of the drawings, and the drawings themselves, disclose at least one preferred embodiment of the invention, and may disclose alternative embodiments of the invention.

All elements claimed in any particular claim are essential to the invention claimed in that particular claim. Consequently, replacement of one or more claimed elements constitutes reconstruction and not repair. Additionally, benefits, other advantages, and solutions to problems have been described with regard to specific embodiments. The benefits, advantages, solutions to problems, and any element or elements that may cause any benefit, advantage, or solution to occur or become more pronounced, however, are not to be construed as critical, required, or essential features or elements of any or all of the claims, unless such benefit, advantage, solution, or element is stated in such claims.

Moreover, embodiments and limitations disclosed herein are not dedicated to the public under the doctrine of dedication if the embodiments and/or limitations: (1) are not expressly claimed in the claims; and (2) are or are potentially equivalents of express elements and/or limitations in the claims under the doctrine of equivalents.

What is claimed is:

1. An ultrasound imaging device configured to facilitate sub-dermal monitoring of a probe inserted into a target zone, the ultrasound imaging device comprising:
    a handheld housing;
    a processor within the handheld housing;
    a transducer assembly coupled to the handheld housing and to the processor;
    a scan converter coupled to the transducer assembly;
    a display coupled to the handheld housing and coupled to at least one of the scan converter or the processor; and
    a rechargeable power source coupled to the handheld housing;
    wherein:
        the transducer assembly comprises:
            a first transducer array coupled to the processor and aligned along a first axis; and
            a second transducer array coupled to the processor and aligned along a second axis different than the first axis;
        the first axis is longitudinal to the target zone;
        the second axis is transverse to the target zone;
        the first transducer array and the second transducer array are substantially perpendicular to each other;
        the first transducer array comprises transducer elements configured to scan along the first axis;
        the second transducer array comprises transducer elements configured to scan along the second axis;
        the rechargeable power source is cordless and configured to power the ultrasound imaging device uninterrupted for at least approximately a half-hour;
        the ultrasound imaging device is configured for single-handed operation;
        the second transducer array is configured to:
            scan a transverse cross-section of the target zone along the second axis;
        the first transducer array is configured to:
            scan a longitudinal cross-section of the target zone along the first axis; and
            detect a probe point depth between the transducer assembly and a probe end of the probe along the longitudinal cross-section;
        and
        the processor is configured to:
            data from the second transducer array about the scan of the transverse cross-section;
            receive data from the first transducer array about the scan of the longitudinal cross-section;
            track movement of a probe point from the data received from the first transducer array;
            determine the probe point depth based on the data from the first transducer array;

present on the display a transverse cross-section view of the transverse cross-section from the scan by the second transducer array; and present on the display, concurrently with the transverse cross-section view, a probe point highlight of the probe point of the probe at a longitudinal coordinate of the transverse cross-section view from the second transducer array, the longitudinal coordinate corresponding to the probe point depth based on the data received from the first transducer array.

2. The ultrasound imaging device of claim 1, wherein:
at least one of the first or second transducer arrays is configured to:
detect a probe width location at the transverse cross-section; and
the processor is configured to present at the display the probe point highlight at a transverse coordinate of the transverse cross-section corresponding to the probe width location.

3. The ultrasound imaging device of claim 2, further comprising:
a switch mechanism coupled to the processor;
wherein:
the switch mechanism and the processor are configured to:
deactivate the second transducer array and activate the first transducer array in response to a first setting of the switch mechanism; and
deactivate the first transducer array and activate the second transducer array in response to a second setting of the switch mechanism;
and
the processor is configured to:
present on the display a longitudinal cross-section view of the longitudinal cross-section scanned by the first transducer array in response to the first setting of the switch mechanism; and
present on the display the transverse cross-section view of the transverse cross-section scanned by the second transducer array in response to the second setting of the switch mechanism.

4. The ultrasound imaging device of claim 3, further comprising:
a communications port coupled to the handheld housing;
wherein:
the communications port is configured to transmit information between the ultrasound imaging device and at least one of a computer or a database; and
the rechargeable power source fits within the handheld housing; and
the handheld housing is configured for one-handed operation.

5. The ultrasound imaging device of claim 1, wherein:
the first transducer array is operable at a first frequency;
the second transducer array is operable at a second frequency substantially non-interfering with the first frequency; and
the first and second transducer arrays are simultaneously operable to present both the transverse cross-section view and the probe point highlight at the display in real time.

6. The ultrasound imaging device of claim 5, wherein:
the processor is configured to operate the first and second transducer arrays at different frequencies such that the first and second frequencies are different from each other.

7. The ultrasound imaging device of claim 1, wherein:
the first and second transducer arrays are alternatingly oscillatable relative to each other such that:
when the first transducer array is activated for scanning along the first axis, the second transducer array is deactivated to cease scanning along the second axis;
when the second transducer array is activated for scanning along the second axis, the first transducer array is deactivated to cease scanning along the first axis; and
when the transverse cross-section view is presented at the display, the transverse cross-section and the probe point highlight are presented in real time.

8. The ultrasound imaging device of claim 1, further comprising:
a proximity indicator; and
the probe;
wherein:
the probe comprises a catheter configured to be routed to a desired location along a vessel;
the catheter comprises a sensor configured to detect a signal generated proximate to the desired location; and
the ultrasound imaging device is configured to actuate the proximity indicator, when the sensor of the catheter detects the signal, to indicate that the catheter has reached the desired location.

9. The ultrasound imaging device of claim 1, further comprising:
the probe;
wherein:
the probe comprises a needle comprising:
an interior surface;
an exterior surface;
a needle tip portion comprising a bevel between the interior surface and the exterior surface; and
one or more indentations configured to enhance ultrasonic beam reflections off the needle tip portion; and
a first indentation of the one or more indentations is located on the bevel of the needle tip portion.

10. A monitoring device configured to facilitate intra-tissue inspection of a probe at a target region, the monitoring device comprising:
a housing;
a processor within the housing;
a transducer coupled to the housing and the processor; and
a display coupled to the processor and to the housing;
wherein:
the transducer comprises:
a first transducer array aligned to scan a longitudinal cross-section of the target region; and
a second transducer array aligned to scan a transverse cross-section of the target region;
the first transducer array is configured to detect a probe point depth of a probe point of the probe along the longitudinal cross-section; and
the processor is configured to:
receive data from the second transducer array about the scan of the transverse cross-section;
receive data from the first transducer array about the scan of the longitudinal cross-section;
track movement of the probe point from the data received from the first transducer array;
determine the probe point depth based on the data from the first transducer array;

present on the display a transverse cross-section view of the transverse cross-section from the scan by the second transducer array; and present on the display, concurrently with the transverse cross-section view, a probe point highlight of the probe point of the probe at a longitudinal coordinate of the transverse cross-section view from the second transducer array, the longitudinal coordinate corresponding to the probe point depth based on the data received from the first transducer array.

11. The monitoring device of claim 10, wherein:
at least one of the first or second transducer arrays is configured to:
detect a probe width location along the transverse cross-section; and
the processor is configured to present, on the display, the probe point highlight at a transverse coordinate of the transverse cross-section view corresponding to the probe width location.

12. The monitoring device of claim 10, wherein:
the first and second transducer arrays are arranged and controlled by the processor such that:
a portion of the scan of the longitudinal cross-section by the first transducer array overlaps with a portion of the scan of the transverse cross-section by the second transducer array.

13. The monitoring device of claim 10, wherein:
the first and second transducer arrays are arranged and controlled by the processor such that:
the scan of the longitudinal cross-section by the first transducer array is non-overlapping with the scan of the transverse cross-section by the second transducer array; and
a portion of the scan of the longitudinal cross-section by the first transducer array is contiguous with a portion of the scan of the transverse cross-section by the second transducer array.

14. The monitoring device of claim 10, wherein:
the transducer is at least partially enclosed by the housing;
the display is at least partially enclosed by the housing;
the first and second transducer arrays are substantially perpendicular to each other; and
the display is substantially parallel to the transverse cross-section.

15. The monitoring device of claim 14, further comprising:
a switch mechanism coupled to the processor;
wherein:
the switch mechanism and the processor are configured to:
deactivate the second transducer array and activate the first transducer array in response to a first setting of the switch mechanism; and
deactivate the first transducer array and activate the second transducer array in response to a second setting of the switch mechanism; and
the display is configured to:
present a longitudinal cross-section view of the longitudinal cross-section in response to the first setting of the switch mechanism; and
present the transverse cross-section view of the transverse cross-section in response to the second setting of the switch mechanism.

16. The monitoring device of claim 10, further comprising:
a communications port coupled to the housing;
wherein the communications port is configured to transmit information between the monitoring device and at least one of a computer or a database.

17. The monitoring device of claim 10, further comprising:
a portable and rechargeable power source coupled to the housing;
wherein the monitoring device is configured for one-handed operation.

18. The monitoring device of claim 10, wherein:
the processor is configured to operate the first transducer array at a first frequency;
the processor is configured to operate the second transducer array at a second frequency substantially non-interfering with the first frequency; and
the processor is configured to operate the first and second transducer arrays simultaneously to simultaneously present both the transverse cross-section and the probe point highlight at the display in real time.

19. The monitoring of claim 10, wherein:
the first and second transducer arrays are alternatingly oscillatable relative to each other such that:
when the first transducer array is activated for scanning along the longitudinal cross-section, the second transducer array is deactivated to cease scanning along the transverse cross-section;
when the second transducer array is activated for scanning along the transverse cross-section, the first transducer array is deactivated to cease scanning along the longitudinal cross-section; and
when the transverse cross-section view is presented at the display, the transverse cross-section and the probe point highlight are simultaneously presented in real time.

20. A method for providing a monitoring device, the method comprising:
providing a housing;
providing a processor within the housing
providing a transducer coupled to the housing and the processor; and
providing a display coupled to the processor and to the housing;
wherein:
providing the transducer comprises:
providing a first transducer array aligned to scan a longitudinal cross-section of a target region, the target region being subdermal; and
providing a second transducer array aligned to scan a transverse cross-section of the target region;
the first transducer array is configured to detect a probe point depth of a probe point of a probe along the longitudinal cross-section; and
the processor is configured to:
receive data from the second transducer array about the scan of the transverse cross-section;
receive data from the first transducer array about the scan of the longitudinal cross-section;
track movement of the probe point from the data received from the first transducer array;
determine the probe point depth based on the data from the first transducer array;
present on the display a transverse cross-section view of the transverse cross-section from the scan by the second transducer array; and
present on the display, concurrently with the transverse cross-section view, a probe point highlight of the probe point of the probe at a longitudinal coordinate of the transverse cross-section view from the second transducer array, the longitudinal coordinate corresponding to the probe point depth based on the data received from the first transducer array.

21. The method of claim 20, further comprising:
providing a power source configured to be coupled with the housing;
wherein:
  the power source is portable and rechargeable; and
  the housing is configured for single-handed operation.

22. The method of claim 20, wherein:
the processor is configured to:
  operate the first transducer array at a first frequency; and
  operate the second transducer array at a second frequency substantially non-interfering with the first frequency; and
  operate the first and second transducer arrays simultaneously to concurrently present both the transverse cross-section view and the probe point highlight at the display in real time.

23. The method of claim 20, wherein:
the processor is configured to:
  operate the first and second transducer arrays to alternatingly oscillate such that:
    when the first transducer array is activated for scanning along the longitudinal cross-section, the second transducer array is deactivated to cease scanning along the transverse cross-section;
    when the second transducer array is activated for scanning along the transverse cross-section, the first transducer array is deactivated to cease scanning along the longitudinal cross-section; and
    when the transverse cross-section view is presented at the display, the transverse cross-section and the probe point highlight are concurrently presented in real time.

24. The method of claim 10, further comprising:
providing the probe;
wherein:
  the probe comprises a needle comprising:
    an interior surface;
    an exterior surface;
    a needle tip portion comprising a bevel between the interior surface and the exterior surface; and
    one or more indentations configured to enhance ultrasonic beam reflections off the needle tip portion; and
  a first indentation of the one or more indentations is located on the bevel of the needle tip portion.

* * * * *